(12) United States Patent
De Strooper et al.

(10) Patent No.: US 9,879,233 B2
(45) Date of Patent: Jan. 30, 2018

(54) RESTORING PHOSPHORYLATION OF A NOVEL PINK1 SUBSTRATE TO TREAT PARKINSON'S DISEASE

(71) Applicants: VIB VZW, Gent (BE); KATHOLIEKE UNIVERSITEIT LEUVEN, K.U.LEUVEN R&D, Leuven (BE)

(72) Inventors: Bart De Strooper, Leuven (BE); Patrik Verstreken, Blanden (BE); Vanessa Morais Epifânio, Kessel-Lo (BE)

(73) Assignees: VIB VZW, Gent (BE); KATHOLIEKE UNIVERSITEIT LEUVEN, Leuven (BE)

( * ) Notice: Subject to any disclaimer, the term of this patent is extended or adjusted under 35 U.S.C. 154(b) by 41 days.

(21) Appl. No.: 14/440,746

(22) PCT Filed: Nov. 7, 2013

(86) PCT No.: PCT/EP2013/073280
§ 371 (c)(1),
(2) Date: May 5, 2015

(87) PCT Pub. No.: WO2014/072412
PCT Pub. Date: May 15, 2014

(65) Prior Publication Data
US 2015/0299672 A1   Oct. 22, 2015

Related U.S. Application Data

(60) Provisional application No. 61/723,705, filed on Nov. 7, 2012.

(51) Int. Cl.
| | |
|---|---|
| *A61K 48/00* | (2006.01) |
| *A01N 63/00* | (2006.01) |
| *C12N 9/02* | (2006.01) |
| *A61K 38/44* | (2006.01) |
| *C12Q 1/32* | (2006.01) |

(52) U.S. Cl.
CPC ............ *C12N 9/0036* (2013.01); *A61K 38/44* (2013.01); *A61K 48/00* (2013.01); *C12Q 1/32* (2013.01); *C12Y 106/05003* (2013.01); *C12Y 106/99003* (2013.01)

(58) Field of Classification Search
CPC .... C12Y 106/05003; C12Y 106/99003; A61K 38/44; A61K 48/00; C12N 9/0036; C12Q 1/32
USPC ........................................................ 514/44 R
See application file for complete search history.

(56) References Cited

PUBLICATIONS

Berry et al Feb. 2011, J. Neurol. 258:179-188.*
Morais et al, 2014, Science 344:203-207.*
Buneeva et al. (2011) "Mitochondrial dysfunction in Parkinson's disease," Biochemistry (Moscow) Supplement Series B: Biomedical Chemistry. 5(4):313-336.
Hoefs et al. (2011) "NDUFA10 mutations cause complex I deficiency in a patient with Leigh disease," European Journal of Human Genetics. 19:270-274.
Matta et al. (Sep. 20, 2012) "LRRK2 Controls an EndoA Phosphorylation Cycle in Synaptic Endocytosis," Neuron. 75:1008-1021.
Morais et al. (2009) "Parkinson's disease mutations in PINK1 result in decreased Complex I activity and deficient synaptic function," Embo Mol. Med. 1:99-111.
Schilling et al. (2005) "Mass spectrometric identification of a novel phosphorylation site in subunit NDUFA10 of bovine mitochondrial complex I," FEBS Letters. 579:2485-2490.
Vilain et al. (Jan. 2012) "The yeast complex I equivalent NADH dehydrogenase rescues pink1 mutants," PLoS One Genetics. 8(1):e1002456. pp. 1-13.
International Search Report with Written Opinion corresponding to International Patent Application No. PCT/EP2013/073280, dated Mar. 24, 2014.

* cited by examiner

*Primary Examiner* — Christopher M Babic
*Assistant Examiner* — Kelaginamane T Hiriyanna
(74) *Attorney, Agent, or Firm* — Lathrop Gage LLP; James H. Velema, Esq.

(57) ABSTRACT

The present application relates to the field of Parkinson's disease (PD), particularly sporadic PD or PD associated with mutations in the mitochondrial kinase PINK1. A new substrate for this kinase, NdufA10, is identified herein. In Parkinson's disease, this protein is dephosphorylated, which is linked to a loss of mitochondrial membrane potential. It is shown that restoring or mimicking phosphorylation of NdufA10 restores the phenotypic defects associated with Parkinson's disease and is thus a new therapeutic paradigm.

9 Claims, 6 Drawing Sheets

RESTORING PHOSPHORYLATION OF A NOVEL PINK1 SUBSTRATE TO TREAT PARKINSON'S DISEASE

RELATED APPLICATIONS

This application is a 35 U.S.C. § 371 filing of International Application No. PCT/EP2013/073280, filed Nov. 7, 2013, which claims priority to U.S. Patent Application No. 61/723,705, filed Nov. 7, 2012, each of which is incorporated herein by reference in its entirety.

FIELD OF THE INVENTION

The present application relates to the field of Parkinson's disease (PD), particularly Parkinson's disease with an important mitochondrial component, such as sporadic PD or PD associated with mutations in the mitochondrial kinase PINK1. A new substrate for this kinase, NdufA10, is identified herein. In Parkinson's disease, this protein is dephosphorylated, which is linked to a loss of mitochondrial membrane potential. It is shown that restoring or mimicking phosphorylation of NdufA10 restores the phenotypic defects associated with Parkinson's disease.

BACKGROUND

Parkinson's disease (PD) is a degenerative disorder of the central nervous system. Most cases are sporadic, although a subset of cases has a genetic origin. Increasing evidence points to a role of mitochondrial dysfunction in many forms of Parkinsonism.

Indeed, mitochondrial toxins, such as MPTP (1-methyl 4-phenyl-1,2,3,6-tetrahydropyridine) and rotenone, but also various defects in the electron transport chain (ETC) are associated with sporadic PD[6,7].

Mutations in PINK1, a mitochondrial targeted Ser/Thr kinase, cause a monogenic form of PD[1,2]. These human mutations, as well as absence of PINK1 in diverse animal models, are associated with ETC deficiencies[3,5,8], supporting the hypothesis that defects in ETC are a major culprit in the pathogenesis of PD. However, no mechanisms have been proposed, and the alternative, not necessarily contradictory, hypothesis that mutations in PINK1 cause PD by interfering with the PARKIN-mediated CCCP-induced mitophagy pathway (clearance of defective mitochondria) has gained ground considerably[9-11]. Defects in mitochondrial clearance are linked to mitochondrial fusion/fission defects[10], which could explain thorax muscle degeneration and flight deficits observed in pink1 and parkin Drosophila models[12-14]. These defects are indeed rescued by expression of the fission promoting gene Drp1 or ablating the fusion promoting gene Opa1, respectively[15,16]. Intriguingly, other pink1-related phenotypes, such as defective neurotransmitter release and loss of mitochondrial membrane potential ($\Delta\psi_m$) in Drosophila neurons, cannot be rescued by fission gene Drp1[17], but by genes restoring the proton motive force[18], or by NDi1, a rotenone-insensitive NADH-quinone oxidoreductase of Saccharomyces cerevisiae[17]. These results confirm that two parallel pathways are affected in pink1B9 null Drosophila, one involved in clearance of defective mitochondria and another in the maintenance of $\Delta\psi_m$. Each pathway might explain a different subset of phenotypes in the fly. In contrast, Pink1[-/-] mice display very subtle, and somewhat controversial, phenotypes of altered mitochondrial morphology in resting state[3,8,19,20], and it is unclear to what extent decreased mitophagy or Complex I deficiency contributes to these defects.

It would be advantageous to identify defects underlying the mitochondrial deficiencies observed in PD. Particularly useful would be if these defects not only can help in diagnosing PD, but also point the way to new therapeutic paradigms.

SUMMARY

Mutations in the mitochondrial kinase PINK1 cause recessively inherited early onset Parkinson's disease (PD)[1,2]. Under resting conditions mouse Pink1 knockout cells and cells derived from patients with PINK1 mutations display a loss of mitochondrial membrane potential, $\Delta\psi_m$, reflecting a primordial role for PINK1 in the regulation of Complex I activity[3-5].

As PINK1 is a kinase, it was reasoned that deficient phosphorylation of one or more specific substrates could underlie this pathologic phenotype. To identify possibly relevant PINK1 substrates, we have analysed the complete phosphoproteome of Complex I in brain and liver from Pink1[+/+] and Pink1[-/-] mice. As will be detailed in the Examples section, a particular subunit of Complex I, NdufA10, was identified as a novel substrate. Specific involvement of PINK1 in the phosphorylation of Ser250 in this subunit could be demonstrated. This is physiologically relevant, as phosphorylation of Ser250 activates ubiquinone reduction by Complex I. Also, a phosphomimetic NdufA10 mutant reverses Pink1 deficits in mouse knockout cells and rescues mitochondrial depolarization and synaptic neurotransmission in pinkB9 null mutant Drosophila. Thus we identify a conserved molecular pathway regulating $\Delta\psi_m$ in Drosophila, mouse and human. Importantly, phosphomimetic NdufA10 rescues the deficit in human cells derived from PINK1 patients. Summarizing, these data reveal a novel mechanism contributing to the pathogenesis of PD. Moreover, as correcting (or mimicking) the phosphorylation of this novel target overcomes the disease phenotype, these results also provide a new therapeutic opportunity in the treatment of PD, particularly PD associated with loss of mitochondrial membrane potential (such as e.g. many cases of sporadic PD, and PD as a result of mutations in PINK1).

Accordingly, it is an object of the invention to provide NdufA10 phosphomimetic mutants, or nucleic acids encoding such phosphomimetic mutants. Also provided herein are nucleic acid expression cassettes, such as nucleic acid vectors, comprising these nucleic acids encoding NdufA10 phosphomimetic mutants. These expression cassettes or vectors allow the transcription and translation of the phosphomimetic proteins in suitable cells (e.g. in cell cultures or host organisms).

According to particular embodiments, the phosphomimetic mutants harbor a phosphomimetic mutation at position 250 (or the equivalent position in a non-human protein). According to further particular embodiments, the mutation is a mutation of a serine residue. According to yet further particular embodiments, the mutation is a S250D mutation. Likewise, the nucleic acids provided herein encode for phosphomimetic mutants with a phosphomimetic mutation at position 250 or equivalent position, particularly the S250D mutation.

According to another embodiment, the phosphomimetic mutants (or nucleic acids encoding the phosphomimetic mutants) are provided for use as a medicament. Particularly, the phosphomimetic mutants (or nucleic acids encoding the phosphomimetic mutants) are provided for use in the treatment of Parkinson's disease. Particularly envisaged forms of Parkinson's disease include, but are not limited to, sporadic Parkinson's disease, Parkinson's characterized by mutations in PINK1, and Parkinson's characterized by mutations in Parkin. Also particularly envisaged is mitochondrial Parkinson's disease (OMIM #556500).

In a further embodiment, methods of diagnosing Parkinson's disease in a subject are provided, comprising determining the phosphorylation status of NdufA10 in a sample obtained from the subject. Particularly envisaged samples include, but are not limited to, brain samples, fibroblasts, muscle tissue, and blood samples. The latter are particularly envisaged, since these are the least invasive to obtain. NdufA10 phosphorylation can be assessed in different ways known by the skilled person, some of which are detailed further in the specification. Phosphorylation status particularly refers to the phosphorylation of the serine at position 250 (or the equivalent serine residue in proteins from non-human subjects), and reduced or absent phosphorylation of this residue is indicative of the presence of Parkinson's disease in the subject. Particularly envisaged forms of Parkinson's disease for diagnosis are the same as those for treatment.

According to a further aspect, methods are provided for treating Parkinson's disease, comprising restoring (or mimicking) the phosphorylation of NdufA10 in said subject, particularly in the brain of the subject, most particularly in the substantia nigra of the subject. Restoring the phosphorylation can be done by e.g. compounds that increase kinase activity exerted on NdufA10 (thus e.g. increase Pink1 kinase activity). It is particularly envisaged however to restore the phosphorylation of NdufA10 by mimicking phosphorylation.

Mimicking phosphorylation of NdufA10 can be achieved by administering a phosphomimetic mutant of NdufA10 to the subject. This can be done e.g. by intrathecal administration of the protein, but typically, it is envisaged to achieve this by means of gene therapy, i.e. by administering a nucleic acid encoding a NdufA10 phosphomimetic mutant to the subject.

Methods of diagnosis and treatment can be combined: when a diagnostic method finds decreased (or absence of) phosphorylation of NdufA10 in a sample of the subject, the decision may be made to treat the subject by restoring (or mimicking) NdufA10 phosphorylation.

According to further aspects, screening methods are provided to screen for compounds able to restore or increase NdufA10 phosphorylation, comprising the steps of:
  contacting a composition comprising
    the NdufA10 protein, or a NdufA10 peptide substrate; and
    a kinase or phosphatase able to affect phosphorylation of NdufA10
  with a compound; and
  evaluating phosphorylation status of NdufA10.

According to particular embodiments, the kinase able to affect phosphorylation of NdufA10 is PINK1.

a and b, Mitochondrial morphology analysis and quantification in fibroblasts of PINK1 patients (L1703 and L2122) and age-matched controls (L2134 and L2132). Following electroporation of cells with mitochondrial targeted RFP, fluorescent visualization and corresponding morphometric analysis was performed using ImagaJ. Absence of PINK1 does not lead to mitochondrial morphological changes. c and d, Analysis and quantification of the mitochondrial membrane potential in these fibroblasts using the potentiometric dye TMRE. Quantification of TMRE fluorescence was performed using ImageJ software. The mitochondrial membrane potential is decreased in the patient derived fibroblasts. Statistical analysis: student t-test; **, p<0.01; *, p<0.05; mean±s.d.; n=100. Scale bar, 10 µm. e and f, Schematic overview of the analysis of Complex I phosphoproteome. Mitochondrial enriched fractions from Pink1+/+ and Pink1−/− mouse brain and liver where treated with 1% DDM and the solubilized mitochondrial protein complexes were immunocaptured using 20 kDa Complex I subunit antibody. The immunocaptured Complex I was further analysed on SDS-PAGE followed by colloidal coomassie staining (f). The visualized protein bands were excised from the gel, digested with trypsin and fractionated by cation exchange chromatography to enrich for phosphopeptides. Phosphopeptides were further analysed on a Nano-LC-LTQ-Orbitrap-MS. g, Alignment of human (SEQ ID NO: 8), mouse (SEQ ID NO: 9) and *Drosophila* (SEQ ID NO: 10) NdufA10 revealed that the identified PINK1 dependent phospho-serine (in magenta) is conserved across species.

Figure 2:
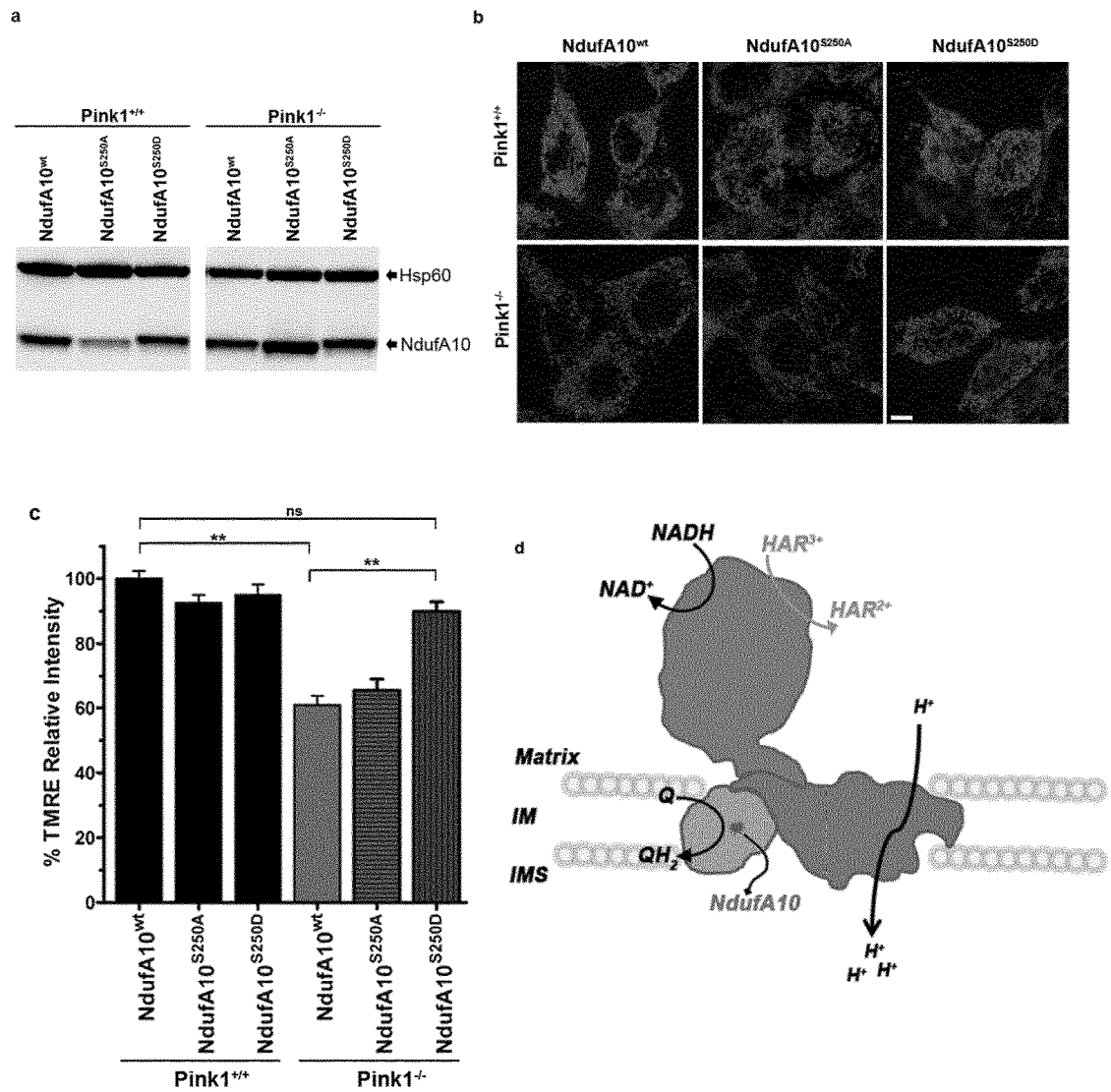
Figure 2:
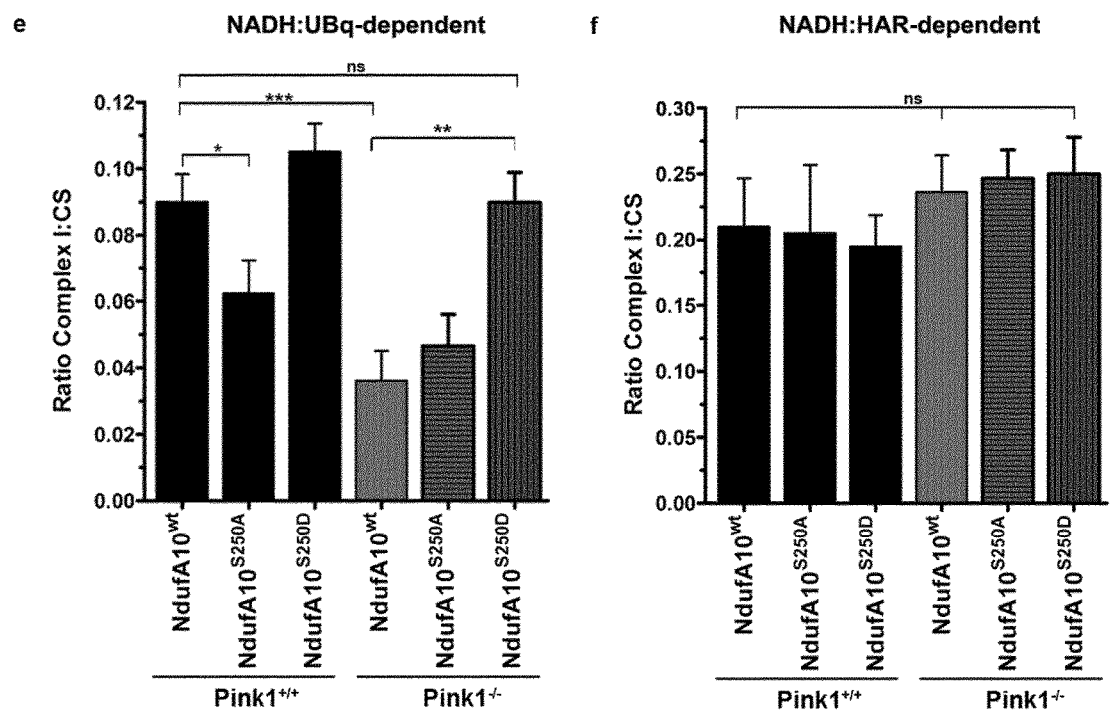

FIG. 2—Expression of phosphomimetic NdufA10 rescues Complex I activity in PINK1 deficient mouse fibroblasts.

a, Pink1+/+ and Pink1−/− MEFs were stably transduced with 3xFLAG-tagged wild type NdufA10wt, phosphorylation-deficient NdufA10S250A and phosphomimetic NdufA10S250D. Expression levels were analysed by Western blotting of mitochondria-enriched fractions using anti-FLAG and anti-Hsp60 (loading control) antibody. b and c, Phosphomimetic NdufA10S250D restores the mitochondrial membrane potential in Pink1−/− MEFs. Cells were stably transduced with NdufA10 constructs as indicated and loaded with 10 nM TMRE (b) and quantification of TMRE intensity (c) over mitochondrial regions of interest was performed using ImageJ software. Statistical analysis: student t-test; , p<0.01; ns, not significant; mean±s.d.; n=100. Scale bar, 10 µm. d, Schematic representation of Complex I. Complex I is composed by 45 different subunits that assemble into a structure of approximately 1 MDa. Electrons that arise from the oxidation of NADH are transferred to a non-covalently bound flavin mononucleotide and sub-sequentially passed through a series of iron-sulfur clusters (Fe—S) finally reaching the acceptor ubiquinone (Q), that is reduced to ubiquinol (QH2). NdufA10 is located in subunit Iγ within the membrane arm domain of Complex I, in close vicinity to the predicted ubiquinone binding pocket. HAR, hexammineritherium. e and f, Analysis of enzymatic function of Complex I. Spectrophotometric assays were performed to measure Complex I (NADH:ubiquinone oxidoreductase) and citrate synthase activities on mitochondria homogenates from Pink1+/+ and Pink11 MEFs rescued with NdufA10 mutants as indicated. In (e), NADH:ubiquinone reduction (rotenone sensitive) and in (f) NADH:HAR reduction were measured. Values were normalized to citrate synthase acitivity. Statistical analysis: student t-test; *; p<0.001; **, p<0.01; *, p<0.05; ns, not significant; mean±s.d.; n=3 independent experiments.

Figure 3:
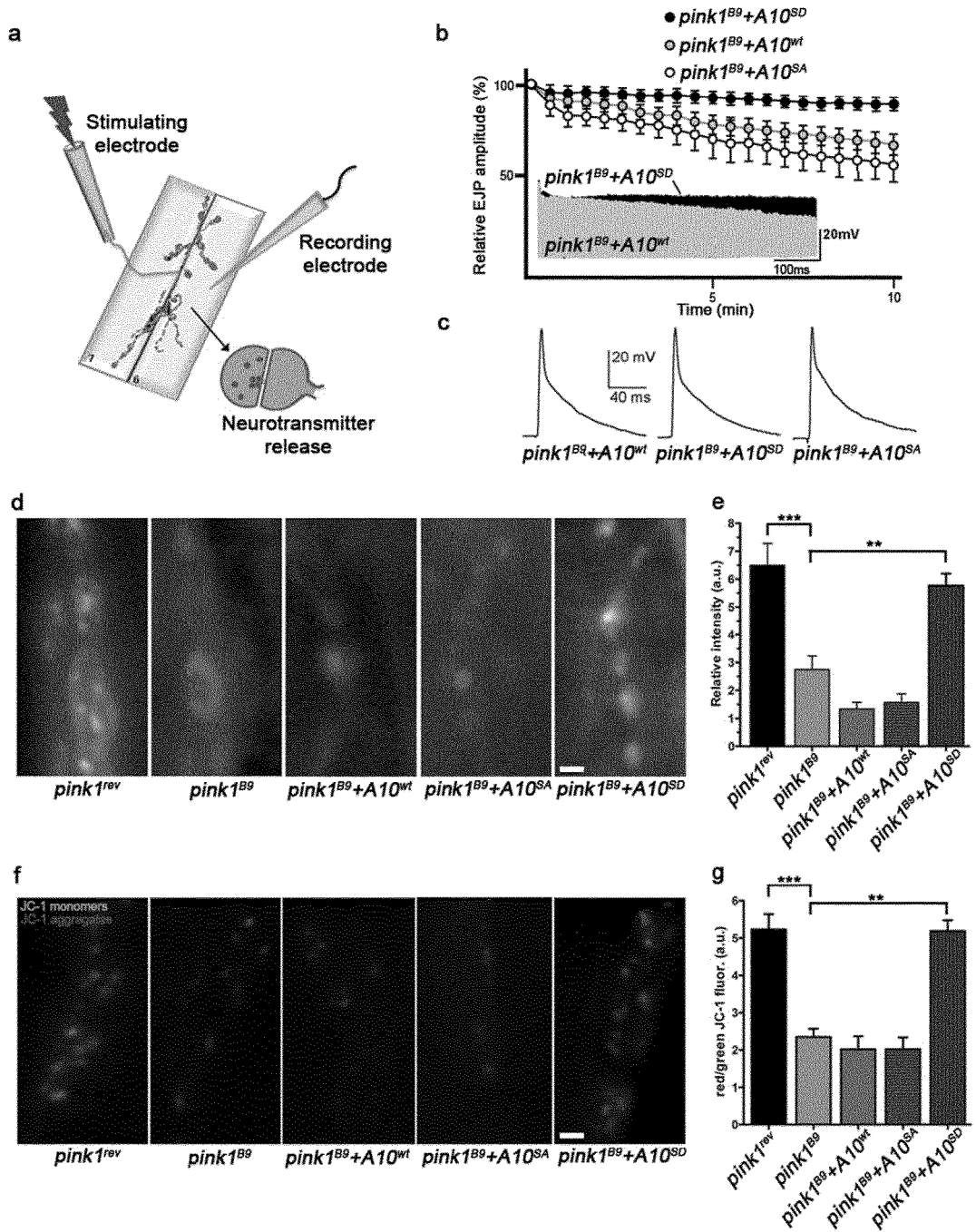

FIG. 3—Restoration of synaptic defects in *Drosophila* pink1B9 null mutants by expressing phosphomimetic NdufA10 a, Schematic representation of a neuromuscular junction (NUJ) from a *Drosophila* third instar larva. The position of the stimulating electrode and nerves, and the recording electrode at muscle 7 and 6, respectively, are illustrated. b, Relative excitatory junction potentials (EJP) amplitudes measured in 2 mM Ca2+ during 10 min of 10 Hz stimulation in pink1B9 null mutants expressing wild type (A10$^{wt}$), phospho-deficient (A10$^{sA}$) and phoshomimetic (A10$^{sD}$) NdufA10 mutants. EJP amplitudes were binned per 30 s and normalized to the average amplitude of the first 15s of recordings. Inset represents an overlay of a raw data trace of EJPs recorded for 10 min at 10 Hz in 2 mM calcium of pink1B9+A10$^{SD}$ (black) and pink1B9+A10$^{wt}$ (grey). The deficit to maintain normal EJP amplitude during a 10 Hz stimulation train observed in pink1B9 mutant expressing A10 wt is restored when phosphomimetic A10SD is present. Mean±s.e.m.; n=4 for A10 wt, 7 for A10SA and 8 for A10SD. c, Depicted traces show basal neurotransmitter release measured at 1 Hz in 2 mM Ca2+ in pink1B9 null mutants expressing NdufA10 mutants. The average EJP amplitudes recorded are: pink1B9+A10wt: 56.4 mV+/−1.9 mV, pink1B9+A10SA: 52.4 mV+/−2.1 mV and pink1B9+A10SD: 57.0 mV+/−3.3 mV. Notice that basal neurotransmitter release is not affected in pink1B9 animals expressing the NdufA10 mutants. d and e, Reserve pool (RP) labelling in controls (pink1REV) and pink1 mutants (pink1B9). Both the exo/endo cycling pool (ECP) and RP were labelled by electrically stimulating motor neurons of third instar filets in the presence of 2 mM Ca2+ for 10 min and then leaving the dye with the preparation for 5 min. ECP and RP vesicles are labelled. Depolarisation with 90 mM KCl, 2 mM Ca2+ and following washing in Ca$^{2+}$ free medium results in unloading of the ECP vesicles but not RP vesicles. Synapses were imaged after this unloading procedure. Quantification (d) of fluorescence intensity of loaded RP vesicles was normalized to loading intensity of controls. Notice that the loading defect in pink1B9 is restored upon expression of phosphomimetic NdufA10. f and g, Imaging of mitochondrial membrane potential in third instar Drosophila larval NMJs in controls (pink1REV) and pink1 mutants (pink1B9) using the ratiometric dye JC-1. For quantification (f), the red JC-1 fluorescence emission to green emission (in the same area) is compared. The mitochondrial membrane potential was restored upon expression of phosphomimetic NdufA10. Statistical analysis: student t-test; *; p<0.001; , p<0.01; *, p<0.05; mean±s.d.; n=8 animals. Scale bar, 4.5 μm.

Figure 4:
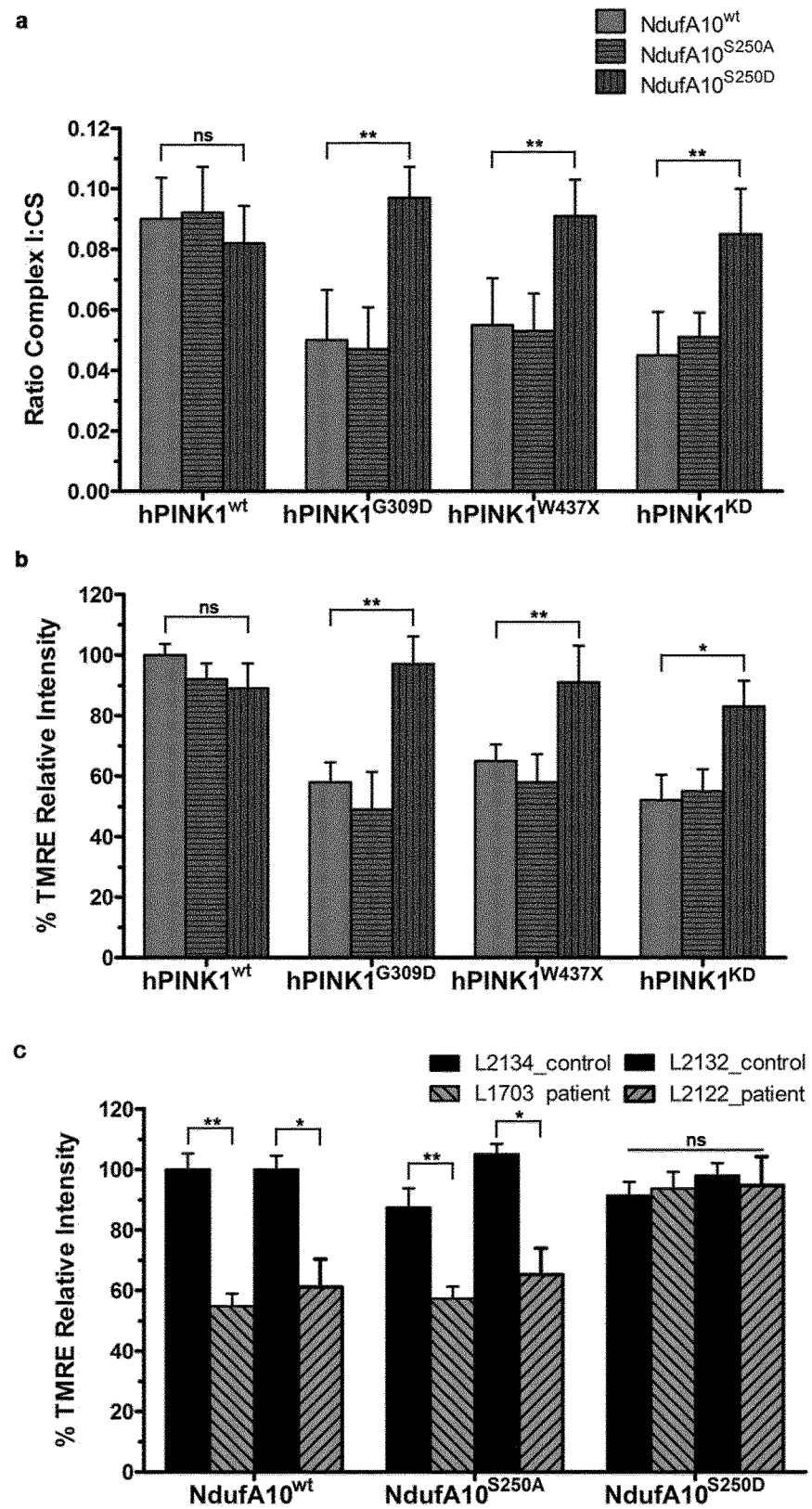

FIG. 4—Restoration of mitochondrial membrane potential in Pink1 deficient MEFs expressing PINK1 PD-causing mutants and PINK1 patient-derived fibroblasts upon expression of phosphomimetic NdufA10.

a, Respiratory chain measurements performed on mitochondria homogenates from Pink1−/− MEFs rescued with human PINK1 wild type (wt) or PD-causing mutants or artificial kinase dead mutant (KD). The cells were stably transduced with NdufA10 phosphomimetic mutants and analysed by spectrophotometric assays for the measurement of Complex I (NADH:ubiquinone oxidoreductase, rotenone sensitive) and citrate synthase enzyme activities. Values were normalized to citrate synthase acitivity. Note that the enzymatic activity of Complex I is rescued in the presence of NdufA10S250D mutant. b, Quantification of mitochondrial membrane potential in the same cell lines. Cells were loaded with 10 nM TMRE and quantification of TMRE intensity over mitochondrial regions of interest was performed using ImageJ software. The mitochondrial membrane potential is restored when phosphomimetic NdufA10$^{S250D}$ is co-expressed. Statistical analysis: student t-test; **, p<0.01; *, p<0.05; ns, not significant; mean±s.d.; for (a) n=3 independent experiments, for (b) n=70. Scale bar, 10 μm. c Quantification of mitochondrial membrane potential in control (L2134 and L2132) and PINK1 patient (L1703 and L2122) fibroblasts electroporated with GFP-tagged NdufA10 mutants loaded with 10 nM TMRE. TMRE fluorescence over mitochondrial regions of interest was quantified using ImageJ software; only cells that were GFP positive were analysed. Statistical analysis: student t-test; **, p<0.01; *, p<0.05; ns, not significant; mean±s.d.; n=80. Scale bar, 10 μm.

Figure 5:
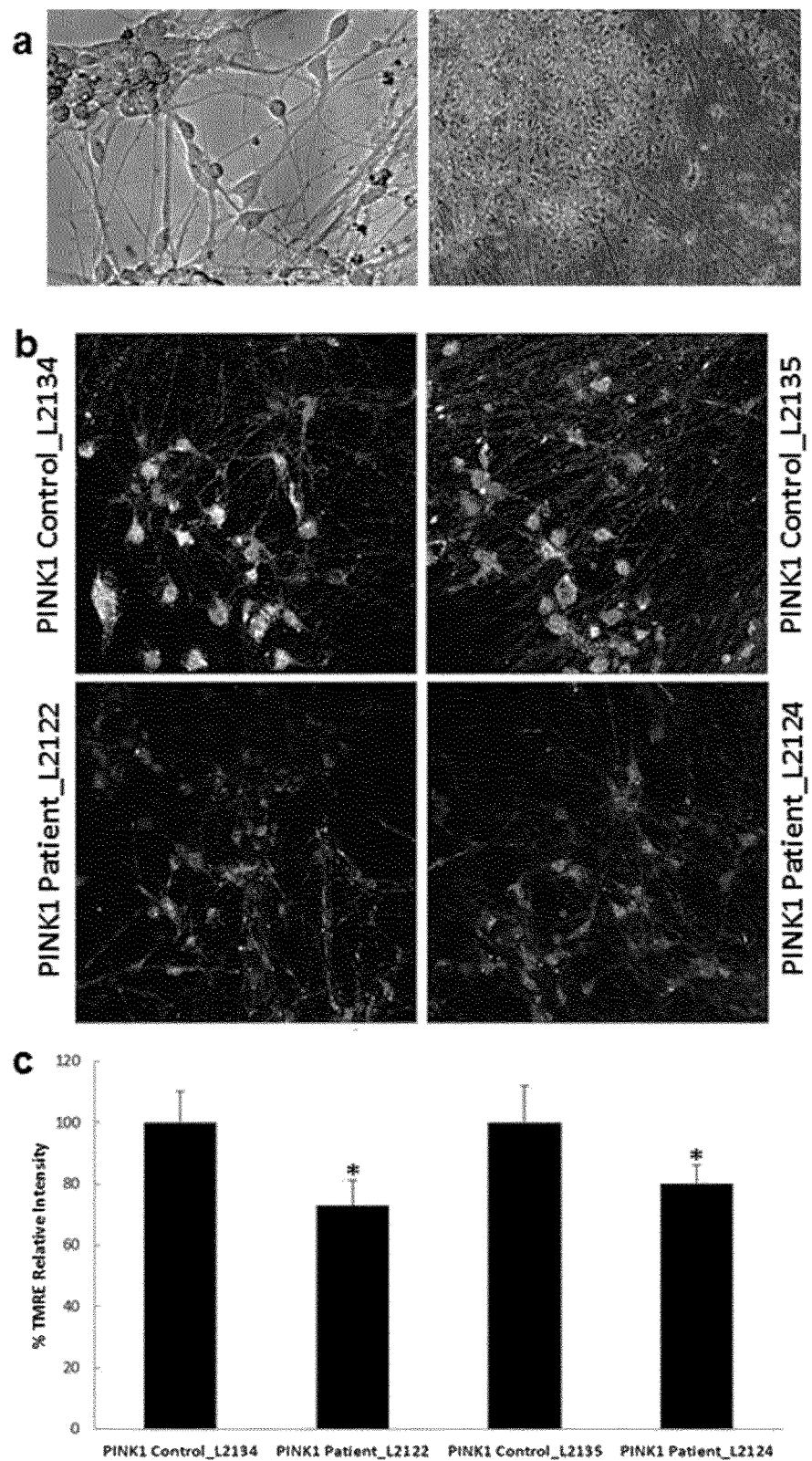

FIG. 5—Human PINK1 patient derived neurons from induced pluripotent stem cells present mitochondrial membrane potential deficits.

a, Generation of iPS cells from a PD patient harboring a PINK1 mutation and a healthy control individual. IPS cells were established from two PD patient with mutant PINK1 (c.1366C>T) and from a healthy family member. Neuronal type morphology is observed in these preparations. b and c, Analysis and quantification of the mitochondrial membrane potential in fibroblasts of PINK1 patients (L2124 and L2122) and age-matched controls (L2134 and L2135) using the potentiometric dye TMRE. Quantification of TMRE fluorescence was performed using ImageJ software. The mitochondrial membrane potential is decreased in the patient derived iPS cells.

Statistical analysis: student t-test; *, p<0.05; mean±s.d.; n=100. Scale bar, 10 μm.

DETAILED DESCRIPTION

Definitions

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

The term "Parkinson's disease" or "PD" as used throughout the application is meant to specifically include mitochondrial forms of Parkinson's disease, grouped as entry

556500 in the OMIM database (Online Mendelian Inheritance in Man, McKusick-Nathans Institute of Genetic Medicine, Johns Hopkins University School of Medicine). This includes sporadic forms of PD as well as genetic forms of PD, e.g. those characterized by mutations in the Pink1 gene.

"Pink1" as used in the application is meant to refer to the gene PTEN induced putative kinase 1 (GeneID: 65018 in humans) or its encoded protein. The gene is also sometimes referred to as PARK6 or BRPK. This gene encodes a serine/threonine protein kinase that localizes to mitochondria. It is thought to protect cells from stress-induced mitochondrial dysfunction. Mutations in this gene are known to cause forms of autosomal recessive early-onset Parkinson disease, grouped as entry *608309 in the OMIM database.

The term "NdufA10" as used herein refers to the gene NADH dehydrogenase (ubiquinone) 1 alpha subcomplex, 10, 42 kDa (Gene ID: 4705 in humans), or its encoded protein. The gene is sometimes also referred to as CI-42kD in the literature. The protein encoded by this gene belongs to the complex I 42 kDA subunit family. Mammalian complex I is the first enzyme complex in the electron transport chain of mitochondria. It is composed of 45 different subunits. NdufA10 is a component of the hydrophobic protein fraction and has NADH dehydrogenase activity and oxidoreductase activity. It transfers electrons from NADH to the respiratory chain.

NdufA10 is a phosphoprotein, meaning that it is a protein that can be phosphorylated at one or more positions. In the context of the application, phosphorylation of NdufA10 typically means serine phosphorylation of the NdufA10 protein. Most particularly, phosphorylation of a particular serine residue is meant. In the human protein (GI:4758768, SEQ ID NO: 1), this is the serine residue at position 250. This serine residue is conserved throughout evolution and is present in species such as *Drosophila* or mice. The skilled person can readily determine the relevant serine residue (or the position thereof) in other species, e.g. using algorithms for sequence alignments such as BLAST. By way of example, in the NdufA10 protein of primates such as chimp (GI:115392071) and gorilla (GI:115502295), it is also at position 250. This is also the case for the protein in horse (GI:149711435). In the protein of dog (GI:345790818), the serine is at position 244; in pig protein (GI:311273371) at position 252; in cattle (GI:28603782) at position 238. In mouse (GI:13195624) and rat NdufA10 protein (GI:170295834), the serine is also at position 250. It should be noted that the proteins of all these mammals show over 75% sequence identity when aligned over their entire length, showing the high evolutionary conservation of these sequences. In more distantly related species, although the overall sequence identity is lower, the serine is nevertheless conserved: in chicken protein (GI:71895153), this is at position 256; in *Xenopus*, both isoforms of the protein (GI:147898604 and GI:148237107) carry the serine at position 246.

As typically used in the application, "phosphorylated NdufA10" means a NdufA10 protein that is phosphorylated at this position (even when the rest of the protein is not phosphorylated), while "dephosphorylated NdufA10" means a protein that is not phosphorylated at that particular serine residue (even when other serine, threonine or tyrosine residues in the protein may be phosphorylated).

Accordingly, the phrase "determining the phosphorylation status" of NdufA10 typically refers to determining whether (or to what extent) this specific residue is phosphorylated. As will be explained further, this can be done directly (by assessing phosphorylation) or indirectly (e.g. by checking for mutations or evaluating an effect depending on the phosphorylation, such as mitochondrial membrane potential).

In some situations, phosphorylation of NdufA10, most particularly serine phosphorylation at the position equivalent to S250 in the human protein, is inadequate or even absent, resulting in physiological defects, most particularly loss of mitochondrial membrane potential $\Delta\psi_m$. In this context, the phrase "restoring the phosphorylation" of NdufA10 refers to increasing the phosphorylation of the NdufA10 protein, most particularly this serine phosphorylation, be it directly or indirectly. This results in an improvement of the physiological symptoms, particularly an improvement in membrane potential. A particular example of restoring the phosphorylation is "mimicking the phosphorylation". This phrase is meant to refer to a situation where the actual phosphorylation levels are not changed, since there is no addition of a phosphate group to the relevant amino acid residue, but the physiological effects of the phosphorylation are achieved by different means. Typically, this is done by substitution of an amino acid (particularly the one that is normally phosphorylated) by another amino acid that has a charge (particularly a negative charge, mimicking the charge of the phosphate group) and/or has increased bulk (mimicking the size of the phosphorylated amino acid residue). Although mimicking the phosphorylation does not effectively add a phosphate group, the physiological effects, particularly the effects on membrane potential, are identical to those obtained with a correctly phosphorylated protein.

The words "a kinase able to affect phosphorylation of NdufA10" as used in the application refers to a kinase the activity of which results in increased phosphorylation of NdufA10 in physiological settings. The latter is important, since NdufA10 is part of a much larger complex, and it can be foreseen that a kinase that is able to phosphorylate purified NdufA10 protein in vitro has no relevant effect in vivo. On the other hand, it should be kept in mind that relevant kinases not necessarily phosphorylate NdufA10 directly. For instance, it is shown herein that the PINK1 kinase affects phosphorylation of NdufA10 in different physiologically relevant contexts, but it cannot be excluded that this is the result of indirect phosphorylation, e.g. through intermediate phosphorylation steps. Nevertheless, since modulating PINK1 activity has effects on the phosphorylation status of NdufA10, PINK1 is explicitly envisaged as a kinase able to affect phosphorylation of NdufA10. For phosphatases able to affect phosphorylation of NdufA10, the same considerations apply mutatis mutandis.

The phrase "peptide substrate of NdufA10" is used herein to refer to a peptide with a site that can be phosphorylated and is recognized by the same kinases/phosphatases that act on NdufA10. Thus, the peptide mimics the NdufA10 substrate. Typically, this is because it is derived from the NdufA10 protein (i.e. its sequence is integrally part of the NdufA10 amino acid sequence). In other words, the peptide provides the same linear epitope as NdufA10. Particularly envisaged linear epitopes are the ones with amino acids that are phosphorylated in vivo, such as the S250 residue. However, peptides that do not have the exact same sequence, but provide the same topology of the phosphosite, i.e. the same conformational epitope as NdufA10, are also envisaged herein. Of course, the linear and conformational epitope embodiments are not mutually exclusive. Phosphorylated sites in NdufA10 are disclosed herein, and others can be found e.g. using PhosphositePlus[32].

The present invention relates to new diagnostic and therapeutic options in the field of Parkinson's disease. According to a first aspect, methods of diagnosing Parkinson's disease in a subject are provided, wherein the methods comprise a step of determining the phosphorylation status of NdufA10 in a sample obtained from the subject.

A 'subject' as used herein refers to a eukaryotic organism, particularly a (individual) mammal, more in particular a human. A sample from said subject may be a fluid sample, e.g. blood, saliva, etc. or a tissue sample, e.g. a tissue biopsy, etc. The sample may be provided as such or can be pre-processed. Although PD is a neurodegenerative disease, the sample is not necessarily a brain sample (although this is also possible). Indeed, the NdufA10 protein is also present in non-brain (peripheral) cells, and the phosphorylation status of NdufA10 can be determined in these other cells (as illustrated for e.g. fibroblasts in the Examples section). Because obtaining samples from other tissues typically is less invasive, these samples are envisaged within the scope of the invention. A particularly envisaged sample is a blood sample, since this is easy to obtain.

Determining or detecting the phosphorylation of NdufA10 can be qualitative (e.g. is the protein phosphorylated or not), semi-quantitative (e.g. is there more or less phosphorylation present) and/or quantitative (e.g. how much of the protein is phosphorylated). As such, the term "quantifying" when used in the context of phosphorylation of a protein in a sample can refer to absolute or to relative quantification. Absolute quantification may be accomplished by inclusion of known concentration(s) of one or more appropriate controls and referencing the detected levels to those of the known controls (e.g. through generation of a standard curve). Alternatively, relative quantification can be accomplished by comparison of detected levels or amounts between samples (or phosphoproteins in a sample) to provide a relative quantification. Evaluating phosphorylation may involve comparison with a positive control (e.g. to assess whether phosphorylation can be detected in the sample, in particular whether the detection method works), a negative control or a blank (typically to assess whether no false positive signal is being generated), one or more standards (either internal or external standards, typically to allow more accurate quantification), or a combination thereof. The positive control may additionally or alternatively be an internal positive control, typically a gene product known to be present in the sample. Detection of expression and/or activity is well known in the art, and a skilled person is capable of choosing appropriate controls and/or standards. Particularly for determining phosphorylation of NdufA10, specific mutants may be used as appropriate controls. For instance, a phosphorylation-deficient NdufA10 mutant (such as e.g. the S250A mutant for the human protein) can be an appropriate negative control, while a phosphomimetic mutant (such as e.g. the S250D mutant for the human protein) can be an appropriate positive control (depending on the read-out).

Phosphorylation can be measured directly (e.g. by an ELISA or equivalent assay measuring the amount of phosphorylated protein), but also indirectly. There are different ways in which NdufA10 phosphorylation can be measured indirectly. For instance, one can look at functional effects of NdufA10 phosphorylation. Examples include, but are not limited to, enzymatic activity of Complex I (this will be decreased if NdufA10 is not properly phosphorylated), overall ATP levels (these will be decreased if NdufA10 is not properly phosphorylated) or mitochondrial membrane potential ($\Delta\psi_m$ will be decreased if NdufA10 is not properly phosphorylated). It should be mentioned here that such assays have been described also for peripheral cells such as blood cells or fibroblasts (e.g. de Wit et al., Methods in Enzymology 2009; 456:169-181; Mitoprofile kit from Invitrogen).

Alternatively, or additionally, one can look at mutations of proteins. If NdufA10 contains a mutation at or near the site to be phosphorylated (e.g. a S250A mutation in the human protein) phosphorylation will be absent or reduced. Likewise, if the PINK1 kinase, which phosphorylates NdufA10, harbours loss-of-function mutations, phosphorylation of NdufA10 will also be absent of reduced. Thus, determining phosphorylation levels of NdufA10 may also comprise evaluating functional effects or assessing the presence of mutations in proteins (particularly PINK1 and/or NdufA10).

The absence or reduction in NdufA10 phosphorylation is indicative of the presence of PD.

According to a further aspect, methods of treating Parkinson's disease in a subject are provided, which methods contain a step of increasing or restoring the phosphorylation of NdufA10 in said subject. Although the phosphorylation may be restored in all cells of the subject, it is particularly envisaged to restore NdufA10 phosphorylation in brain cells (particularly neurons), since Parkinson's is a neurodegenerative disease. According to further particular embodiments, NdufA10 phosphorylation is increased or restored in the substantia nigra of the subject.

Of note, both the diagnosis and treatment methods may be combined into a single method. According to these embodiments, the methods comprise a step of determining the phosphorylation status of NdufA10 in a sample obtained from a subject, and, if the phosphorylation is reduced or absent, restoring the phosphorylation of NdufA10 in said subject.

Correcting or restoring the phosphorylation of NdufA10 may be achieved in different ways. For instance, phosphorylation may be restored by administration of protein, either directly or through nucleic acid encoding the protein. According to particular embodiments, restoring the phosphorylation of NdufA10 is done through gene therapy. Briefly, gene therapy is the use of DNA as a pharmaceutical agent to treat disease and it typically entails the insertion of a nucleic acid to be expressed (often referred to as transgene) in cells of the subject undergoing the gene therapy.

The term 'transgene' as used herein refers to particular nucleic acid sequences encoding a polypeptide or a portion of a polypeptide to be expressed in a cell into which the nucleic acid sequence is inserted. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, anti-sense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is inserted. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions.

In gene therapy, DNA that encodes a therapeutic protein is packaged within a vector, which is used to get the DNA inside cells within the body. Once inside, the DNA becomes expressed by the cell machinery, resulting in the production of therapeutic protein, which in turn treats the patient's disease. Thus, typically, transgenes are provided on a vector. The term 'vector' as used in the application refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. The vectors can be episomal vectors (i.e., that do not integrate into the genome of a host cell), or can be vectors that integrate into the host cell genome. Examples of episomal vectors include (extrachromosomal) plasmids and so-called mini-circles, which are composed of the expression cassette only and are devoid of bacterial sequences, and examples of vectors that integrate into the host cell genome include e.g. retroviral vectors. Vectors may contain additional elements that target them to a particular tissue, especially in case that expression is particularly desired in a given tissue. In the context of the present invention, vectors that target the brain (or are adapted for expression of proteins in the brain) are particularly envisaged.

The most common form of gene therapy involves using DNA that encodes a functional, therapeutic gene in order to replace a mutated gene. Other forms involve directly correcting a mutation, or using DNA that encodes a therapeutic protein drug (rather than a natural human gene) to provide treatment.

In cases where the lack of phosphorylation of NdufA10 is due to a mutation in NdufA10, gene therapy may be done with a gene encoding for a wild type NdufA10. In cases where lack of phosphorylation of NdufA10 is due to defects in function and/or expression of PINK1 kinase, gene therapy with a wild type Pink1 gene is more appropriate.

A particular form of gene therapy that is envisaged however, is gene therapy with a phosphomimetic mutant of NdufA10. This has the advantage of restoring (or rather mimicking) the phosphorylation of NdufA10 regardless of the underlying defect. Although a phosphomimetic mutant does not restore phosphorylation sensu strictu, the phosphomimetic protein shares functions with the phosphorylated protein that the phosphorylation-deficient protein does not have. In other words, the phosphomimetic protein displays at least part of the physiological effects associated with the phosphorylated protein.

Accordingly, in a further aspect of the invention, a NdufA10 phosphomimetic mutant is provided. According to specific embodiments, the phosphomimetic mutant is a mutant of a serine residue in NdufA10. According to further specific embodiments, the serine residue is the serine residue equivalent to the serine at position 250 of the human protein (SEQ ID NO: 1). Which serine residue this is in proteins from other species can easily be determined by the skilled person, e.g. using alignment algorithms. According to particular embodiments, the phosphomimetic mutant is obtained through substitution of the phosphorylated residue (i.e. typically the serine residue) with a negatively charged amino acid residue (to mimic the negative charge of the phosphate group), such as aspartic acid (D) or glutamic acid (E). According to most particular embodiments, the NdufA10 phosphomimetic mutant is characterized by a substitution of serine with aspartic acid at position 250 (or the equivalent position), typically designated herein as NdufA10 S250D.

According to specific embodiments, these phosphomimetic mutants are provided for use as medicament. According to more specific embodiments, these phosphomimetic mutants are provided for use in the treatment of Parkinson's disease.

This is equivalent as stating that methods are provided for treating Parkinson's disease, comprising administering a phosphomimetic mutant to a subject in need thereof.

Although it is envisaged to treat Parkinson's disease in general, specific forms of PD that are envisaged are sporadic Parkinson's disease, Parkinson's characterized by mutations in PINK1 kinase, or Parkinson's characterized by mutations in Parkin. All of these forms of Parkinson's have been linked to mitochondrial dysfunction. Particularly envisaged forms of Parkinson's are those where the mitochondrial dysfunction is characterized by loss of mitochondrial membrane potential (or characterized at least by loss of $\Delta\psi_m$). This is documented best for PD characterized by mutations in PINK1 kinase, or for sporadic PD with defective oxidative phosphorylation.

Of note, since it is particularly envisaged to use the phosphomimetic NdufA10 mutant in methods of gene therapy, also provided are nucleic acids encoding such NdufA10 mutant, and expression vectors containing such nucleic acids. Most particularly, the expression vectors are suitable for use in gene therapy. These nucleic acids and expression vectors are also provided for use as a medicament, particularly for use in the treatment of PD.

Again, this is equivalent as saying that methods are provided for treating Parkinson's disease, comprising administering a nucleic acid encoding a NdufA10 phosphomimetic mutant (or an expression vector containing such nucleic acid) to a subject in need thereof.

Thus, the nucleic acids and the vectors described herein can be used in gene therapy. Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

According to a particular embodiment, the use of the nucleic acids or expression vectors as described herein is envisaged for gene therapy of brain cells. According to a further particular embodiment, the use of the regulatory elements, expression cassettes or vectors is for gene therapy in vivo. According to yet a further particular embodiment, the use is for a method of gene therapy to treat PD.

Apart from gene therapy or protein therapy to restore or mimic the phosphorylation of NdufA10 and thus treat PD, also compounds may be used to restore NdufA10 phosphorylation. Such compounds may have a direct effect on NdufA10 phosphorylation, or may act indirectly. For instance, compounds that increase the activity of PINK1 kinase will also increase the phosphorylation of NdufA10. On the other hand, compounds that inhibit dephosphorylation of NdufA10, by inhibiting a phosphatase acting on NdufA10, will also increase phosphorylation of NdufA10.

According to a further aspect, screening methods are provided to identify compounds able to restore or increase NdufA10 phosphorylation.

Such screening methods can be set up in different ways, as the skilled person will be well aware of. According to a first set-up, compounds can be screened for that increase the activity of a kinase that phosphorylates NdufA10. Methods according to this embodiment typically will entail the contacting of a composition comprising the NdufA10 protein (or a peptide substrate) and a kinase able to affect phosphorylation of NdufA10 with a compound, and evaluating phosphorylation status of NdufA10. As mentioned, instead of using the NdufA10 protein, a peptide substrate can be used. This substrate mimics the relevant NdufA10 substrate, but has the advantage that it is more amenable to screening procedures (e.g. using ELISA). Also, since NdufA10 is part of a complex, the isolated protein may not accurately reflect the physiological situation. Therefore, it may be more relevant to screen using the entire Complex I substrate (but this is challenging, particularly in vitro), or using a peptide that mimics the substrate, in sequence (i.e. linear epitope) and/or in structure (i.e. conformational epitope). A particularly envisaged kinase that can be used in these assays is PINK1, since PINK1 function increases phosphorylation of NdufA10.

The reverse approach is also possible: rather than screen for compounds that increase phosphorylation, screen for compounds that decrease dephosphorylation, e.g. by inhibiting a phosphatase that dephosphorylates NdufA10. Methods according to this embodiment typically will entail the contacting of a composition comprising the NdufA10 protein (or a peptide substrate) and a phosphatase able to affect phosphorylation of NdufA10 with a compound, and evaluating phosphorylation status of NdufA10. As mentioned, instead of using the NdufA10 protein, a peptide substrate can be used. This substrate mimics the relevant NdufA10 substrate, but has the advantage that it is more amenable to screening procedures (e.g. using ELISA). Also, since NdufA10 is part of a complex, the isolated protein may not accurately reflect the physiological situation. Therefore, it may be more relevant to screen using the entire Complex I substrate (but this is challenging, particularly in vitro), or using a peptide that mimics the substrate, in sequence (i.e. linear epitope) and/or in structure (i.e. conformational epitope).

It goes without saying that the skilled person is capable of picking the appropriate NdufA10 form (or relevant peptide substrate) for each assay. E.g., when one wants to increase phosphorylation, it is appropriate to screen using a dephosphorylated NdufA10 substrate. When dephosphorylation is studied, it makes more sense to use a phosphorylated substrate.

According to further embodiments, the restoration or increase in NdufA10 phosphorylation can be screened for indirectly, by screening for a functional result of said phosphorylation. Since NdufA10 is part of Complex I, and the phosphorylation of NdufA10 is essential for correct functioning of Complex I, an increase of NdufA10 phosphorylation will result in increased Complex I enzymatic activity. Methods according to this embodiment will typically entail the contacting of a composition comprising complex I with a compound, and evaluating Complex I enzymatic activity upon contact with the compound.

Typical examples of compositions that contain Complex I include, but are not limited to, cellular or mitochondrial preparations. Particularly envisaged compositions are those that also contain relevant kinases (i.e. those kinases able to affect phosphorylation of NdufA10, such as Pink1) or relevant phosphatases, in addition to containing NdufA10 (which they do by default, since the protein is a part of Complex I). These compositions more closely resemble the physiological situation. Methods to measure Complex I activity have been described in the art. Examples include, but are not limited to, spectrophotometric assays as described e.g. in Janssen et al., Clinical Chemistry 2007; 53 (4): 729-734; Bénit et al., Clin Chim Acta. 2006; 374(1-2): 81-6; or de Wit et al., Methods in Enzymology 2009; 456: 169-181.

Another way in which increase or restoration of NdufA10 phosphorylation levels can be screened for indirectly, is by evaluating ATP levels or mitochondrial membrane potential. Indeed, mitochondria are essential for neuronal function and survival. Energy-demanding neurons require large numbers of functional mitochondria to provide most of their ATP via oxidative phosphorylation, a process where electrons traversing the electron transport chain (complexes I-IV) are coupled to proton pumping to establish a mitochondrial membrane potential subsequently used to synthesize ATP (complex V). Thus, increasing NdufA10 phosphorylation will result in increased ATP production by complex V, and will result in increased $\Delta\psi_m$.

Accordingly, methods are provided that entail contacting a composition comprising cells (e.g. a cellular sample, or the cellular fraction of a sample) with a compound and evaluating the overall ATP levels, or more particularly, the mitochondrial ATP levels. Particularly envisaged as compositions or samples are mitochondrial samples, or mitochondrial fractions of samples, as they allow a more direct way of evaluating mitochondrial ATP levels. Particularly envisaged compositions are those that also contain relevant kinases (i.e. those kinases able to affect phosphorylation of NdufA10, such as Pink1) or relevant phosphatases, in addition to containing NdufA10. Methods of measuring mitochondrial ATP levels have been described in the art, e.g. by Drew and Leeuwenburgh, Am J Physiol Regul Integr Comp Physiol. 2003; 285(5):R1259-67.

It is envisaged, particularly but not exclusively in cases where overall ATP levels are used as a read-out, that an additional step is incorporated in the screening procedure involving evaluation of Complex V activity. This can be done for all compounds or, more economical, only for those that result in an increase in ATP levels. The evaluation of increased Complex V activity ensures that the compounds indeed act on the mitochondrial level. Methods of evaluating complex V activity are known in the art (see also the paragraph above on evaluating complex I activity).

According to further embodiments, screening methods are provided that evaluate an increase or restoration of NdufA10 phosphorylation levels by evaluating the increase in mitochondrial membrane potential. Typically, such methods will entail contacting a composition comprising mitochondria with a compound and evaluating $\Delta\psi_m$. These compositions typically are compositions of cells (or containing cells), or mitochondrial fractions of cellular composition. Particularly envisaged compositions are those that also contain relevant kinases (i.e. those kinases able to affect phosphorylation of NdufA10, such as Pink1) or relevant phosphatases, in addition to containing NdufA10. Typical ways in which mitochondrial membrane potential may be evaluated include, but are not limited to, staining (e.g. using JC-1 dye) or FACS analysis of TMRE (tetramethylrhodamine, ethyl ester) uptake (e.g. using the TMRE-Mitochondrial Membrane Potential Assay Kit of Abcam).

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Material and Methods

For PINK1 patient material, human fibroblasts harbouring the homozygous p.Q456X nonsense mutation (L2122) and the homozygous p.V170G missense mutation (L1703) and age-matched controls (L2134, L2132) were used. For Complex I phosphoproteome, immunocaptured Complex I from mouse brain and liver was analysed by LC-MS/MS. NdufA10 cDNA was obtained from Origene and phosphomimetic mutants were constructed using the multisite-directed mutagenesis kit as described by supplier's protocol (Stratagene), where Ser250 was mutated to either an Alanine (phospho-deficient mutant) or to a Glutamate (phosphomimetic mutant). For mitomorphic analysis, cells were electroporated with a mitochondrial targeted RFP. For determination of mitochondrial membrane potential, TMRE and JC-1 were used on MEFs or third instar larvae, respectively. For Complex I enzymatic assays, spectrophotometric measurements were performed on mitochondrial homogenates from fibroblast cells where either decylubiquinone (NADH: ubiquinone oxidoreductase, rotenone sensitive) or with hexamminerithenium (HAR) were used as Complex I substrates.

Antibodies used: mouse anti-Flag (1:1000), mouse anti-Hsp60 (1:5000); mouse anti-CV subunit. For *Drosophila* genetics, pink1B9 null and pink1rev mutants were crossed with transgenic UAS-(CG6343) (wild type; A10wt). UAS-CG6343S-A (phospho-deficient; A10SA) and UAS-CG6343S-D (phosphomimetic; A10SD) flies (CG6343; dNdufA10; ND-42). Experiments were performed on the following genotype: w pink1B9/Y; UAS-CG6343/+; daGal4/+ and pink1rev/Y; UAS-CG6343/+; daGal4/+.

Electrophysiology was performed on third instar larvae where basal neurotransmitter release was measured at 1 Hz in 2 mM Ca2+ and relative excitatory junction potentials (EJP) amplitudes were measured in 2 mM Ca2+ during 10 min of 10 Hz stimulation. Reserve pool mobilization was performed using FM 1-43 dye.

Site-Directed Mutagenesis and Generation of Stable Cell Lines.

Pink1−/− MEFs stably transduced with PINK1 PD-causing mutations (G309D; W437X), and the artificial kinase inactive mutant (K219S) were previously described (Morais et al., EMBO Mol Med 2009; 1:99-111). Mouse NdufA10 cDNA was obtained from Origene (USA), and for detection purposes a 3×FLAG-tag or a GFP-tag was inserted. NdufA10 mutants were constructed using the multisite-directed mutagenesis kit as described by supplier's protocol (Stratagene), where Serine250 was mutated to either an Alanine (phosphor-deficient mutant) or to a Glutamate (phosphomimetic mutant). To generate stable cell lines, MEFs were transduced using a replication-defective recombinant retroviral expression system (Clontech) and where selected based on their acquired hygromycin resistance.

Human Fibroblasts Derived from PINK1 PD-Causing Mutations.

Human fibroblasts harbouring the homozygous p.Q456X nonsense mutation (L2122) and the homozygous p. V170G missense mutation (L1703) and age-matched controls (L2134, L2132) were previously described (Grunewald et al., Exp Neurol 2009; 219:266-273). Where indicated human fibroblasts were electroporated with GFP-tagged NdufA10 mutants using the NEON system (Invitrogen) according to the supplier's protocol.

Human iPS Cells.

The PINK1 derived iPS cells were obtained according to the previously described protocol[31].

Morphometric Analysis.

Human derived fibroblast cells were electroporated with mitochondrial targeted red fluorescent protein (mtRFP) corresponding to pDsRed2-Mito obtained from Clontech (Mountain View, Calif.) using the NEON system (Invitrogen) according to the supplier's protocol. For epifluorescent imaging of the mitochondrial network, 48 h post-transfection medium was replaced with Hanks balanced salt solution (HBBS) and 10 mM HEPES and cells were placed on the stage of an Olympus IX81 inverted microscope equipped with a CellR imaging system (Olympus). Cells were excited using a 525±20 nm excitation filter and emitted light was collected using a 40×1.4 NA Plan Apo objective (Olympus). Morphometric analysis was performed using ImageJ software as previously described (Cipolat et al., PNAS 2004; 101:15927-15932).

Mitochondrial Isolation and Complex I Immunocapture.

Mitochondria were isolated from Pink1+/+ and Pink1−/− mice by standard differential centrifugation and resuspended in Isolation buffer (IB: 0.2M sucrose, 10 mM Tris-MOPS pH 7.4, 0.1 mM EGTA-Tris pH 7.4) as previously described (Frezza et al., Nat Protocol 2007; 2:287-295). Complex I was immunocaptured from mitochondrial enriched fraction treated with 1% DDM according to manufacturer's protocol (Mitoscience).

LC-MS/MS Analysis.

After elution in 1% SDS, immunocaptured Complex I was analysed on an SDSPAGE followed by coomassie staining. The gel lanes were cut into 15 slices, and these gel slices were then washed with water, followed by acetonitrile/water (1/1, v/v) and acetonitrile, and then vacuum dried. The dried gel slices were then re-swollen in 10% acetonitrile and 50 mM ammonium bicarbonate (pH 8) containing 0.1 µg sequencing-grade modified trypsin (Promega, Madison, Wis., USA). Digestion was allowed to proceed overnight at 37° C. After digestion, the generated peptide mixtures were vacuum-dried and re-dissolved in 20 µl of 2% acetonitrile and 0.1% TFA. These peptide mixtures were then analyzed on an Ultimate 3000 HPLC system (Dionex, Amsterdam, The Netherlands) in-line connected to an LTQ Orbitrap Velos mass spectrometer (Thermo Electron, Bremen, Germany). Here, a 30 min gradient of 2% acetonitrile to 50% acetonitrile, followed by a washing and re-equilibration step, on an in-house packed 15 cm long and 75 urn inner diameter column (Reprosil-Pur Basic C18-HD 3 µm, Dr. Maisch, Germany) was used. Per LC-MS/MS analysis, 2.5 µl of the peptide mixture was consumed. Instrument settings for LC-MS/MS analysis and the generation of MS/MS peak lists were as previously described (Ghesquiere et al., Mol Cell Proteomics 2009; 8:2642-2652). These MS/MS peak lists were then searched using the Mascot Daemon interface (version 2.3.0, Matrix Science, London, UK). The Mascot search parameters were as follows. The spectra were searched in the mouse subsection of the Swiss-Prot database. Acetylation of the protein N-terminus, pyroglutamate formation of N-terminal glutamine, methionine oxidation to methionine-sulfoxide, propionamide formation of cysteine and phosphorylation of serine, threonine and tyrosine were set as variable modifications. The protease was set to trypsin with one missed cleavage allowed. The mass tolerance on the precursor ion was set to ±10 ppm and on fragment ions to ±0.5 Da. In addition, Mascot's C13 setting was set to 1. Only peptides that were ranked one and had an ion score at least equal to the corresponding identity threshold at 99% confidence were withheld and further data handling was done in the ms_lims database (Helsens et al., Proteomics 2010; 10:1261-1264).

Respiratory Assays.

Oxidative phosphorylation complex measurements performed on mitochondrial homogenates from fibroblast cells were analysed by spectrophotometric assays as previously described (de Paepe et al., Pediatr Res 2006; 59:2-6; Sled and Vinogradov, BBA 1193; 1141:262-268). Briefly, measurements of Complex I were performed with either decylubiquinone (NADH:ubiquinone oxidoreductase, rotenone sensitive) or with hexamminerithenium (HAR). The protein concentration was in the range of 2-4 mg/ml. Values were plotted according to the ratio between the specific complex's activity and citrate synthase activity.

Immunohistochemistry.

Primary antibodies used: mouse anti-CV subunit (Mitosciences) was used at 1:500. Secondary antibodies: Alexa-488 conjugated antibodies (Invitrogen) was used at 1:1000.

Western Blot Analyses.

Primary antibodies used: mouse anti-FLAG 1:1000, mouse anti-Hsp60 1:5000 (BD laboratories). Secondary antibodies: anti-rabbit HRP conjugated and anti-mouse HRP conjugated (Bio-Rad) 1:10000.

*Drosophila* Genetics.

Flies were kept on standard molasses medium. w pink1REV controls and w pink1B9 flies were kindly provided by Jeehye Park and Jongkyeong Chung (Korea Advanced Institute of Science and Technology) (Park et al., Nature 2006; 441:1157-1161) and mutant larvae were selected using GFP balancers.

Generation of UAS-CG6343 Transgenic Flies.

dNDUFA10 (CG6343) cDNA was ordered from DGRC (*Drosophila* Genomics Resource Center) DGC (*Drosophila* Gold Collection) clone LD29280 and cloned with 5'-CAGAATTCCAAAATGACCGCCGTGTTCCGCG-3' (SEQ ID NO:2) and 5'-GTGCGGCCGCCTAGTGGTGATGGT-GATGATGGATGCCCTGGTTGATGCCTATTTTC-3' (SEQ ID NO:3) using 2×BIO-X-ACT Short Mix (BIOLINE), cloned in the EcoR1 and Not1 site of pUAST-Attb (PMID: 17360644) and sequenced (A10wt). UAS-CG6343S-A (A10SA) and UAS-CG6343S-D (A10SD) were generated similarly, with the following primers to introduce point mutations for S-A: 5'-CGGCATGGGTGGCGAT-GTCCTTG-3' (SEQ ID NO:4) and 5'-CAAGGACATCGC-CACCCATGCCG-3' (SEQ ID NO:5) and for S-D: 5'-CG-GCATGGGTGTCGATGTCCTTG-3' (SEQ ID NO:6) and 5'-CAAGGACATCGACACCCATGCCG-3' (SEQ ID NO:7). Transgenic flies were created at GenetiVision Inc. (Houston, USA) using PhiC31 mediated transgenesis in the VK1 docking site (2R, 59D3) (PMID: 17138868).

For *Drosophila* genetics, pink1B9 null and pink1rev mutants were crossed with transgenic UAS-(CG6343) (wild type; A10wt). UAS-CG6343S-A (phospho-deficient; A10SA) and UAS-CG6343S-D (phosphomimetic; A10SD) flies (CG6343; dNdufA10; ND-42). Experiments were performed on the following genotype: w pink1B9/Y; UAS-CG6343/+; daGal4/+ and pink1rev/Y; UAS-CG6343/+; daGal4/+.

Imaging of Mitochondrial Membrane Potential.

The dye TMRE was used to evaluate mitochondrial membrane potential. Human fibroblasts and MEFs were grown in 3 cm plastic dishes with glass coverslips (Nunc) and treated with 10 nM TMRE for 10 min at 37° C. as previously described (Narendra et al., Autophagy 2009; 5:706-708). TMRE fluorescence intensity was measured using the ImageJ software. Third instar larval fillets were labelled with JC-1 (Molecular Probes) as described (Verstreken et al., Neuron 2005; 47:365-378). Images were captured on a Nikon FN-1 microscope with a DS-2MBWc digital camera, 63× water objective, NA 0.8 and quantification of labelling intensity was performed using NIS-Elements software.

Electrophysiology.

Larval electrophysiological recordings were performed as described (Verstreken et al., Neuron 2005; 47:365-378; Verstreken et al., Neuron 2003; 40:733-748). Data was recorded with a Multiclamp 700B amplifier (Molecular Devices) and stored using pClamp 10. A 2 mM Ca2+ concentration was used.

FM1-43.

FM 1-43 labelling and unloading were performed as described11. Images were captured on a Nikon FN-1 microscope with a DS-2MBWc digital camera, 63× water objective, NA 0.8 and quantification of labelling intensity was performed using NIS-Elements software.

Statistical Analysis.

The statistical significance of differences between a set of two groups was evaluated using student two-tailed unpaired t-tests (*, p<0.05; , p<0.01; *, p<0.001) in GraphPad Prism (Ghesquiere et al., Mol Cell Proteomics 2009; 8:2642-2652). Mean was calculated using standard deviation (s.d.) or standard error (s.e.m.).

Example 1. Identification of a PINK1 Substrate in Complex I

Figure 1:
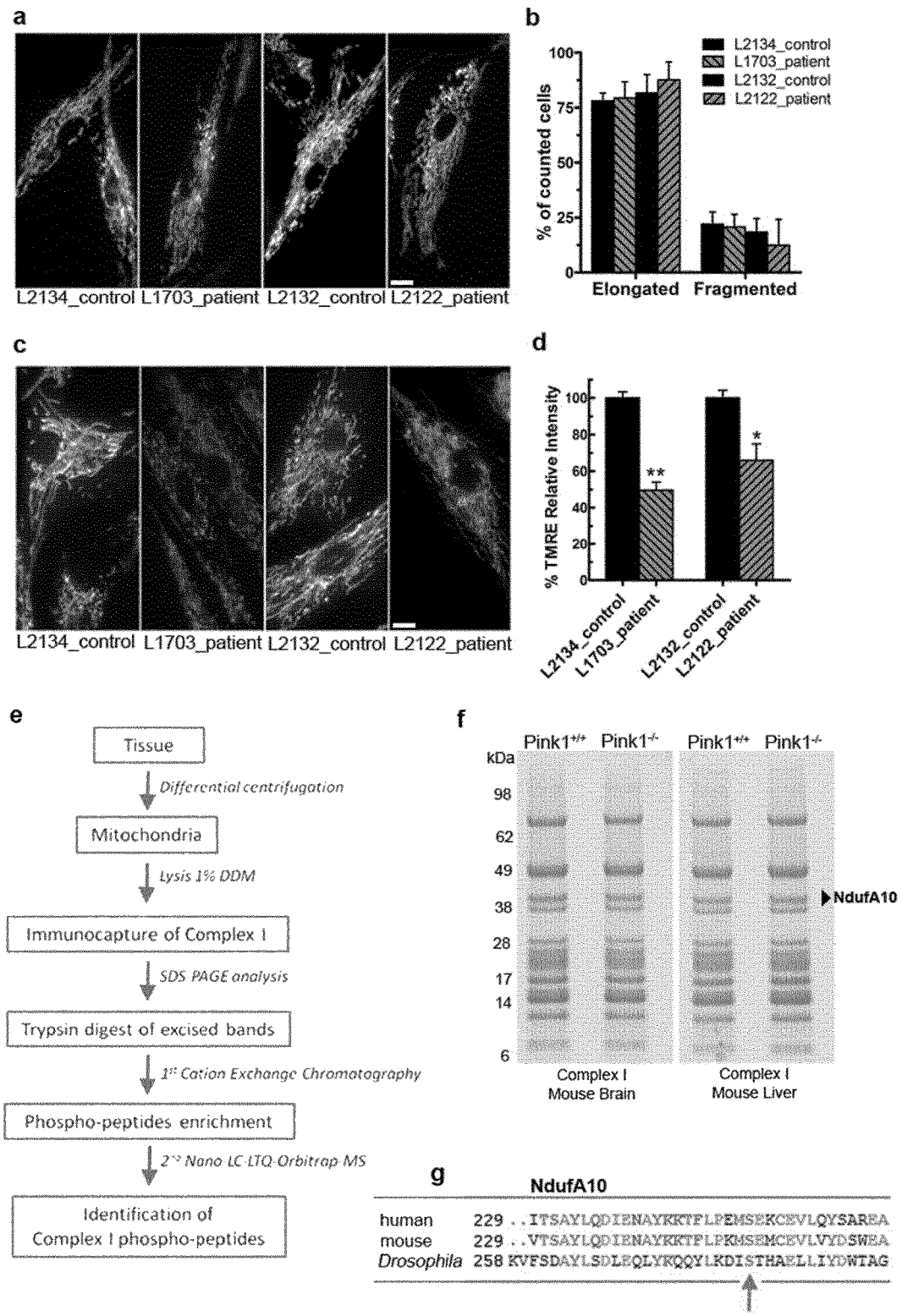
FIG. 1—Human PINK1 patient derived fibroblasts present mitochondrial membrane potential deficits.

We first sought to confirm that clinically relevant mutations in PINK1 affect ETC function. Previously, we reported $\Delta\psi_m$ defects in Pink1 deficient mice and *Drosophila* mutants, which could not be rescued by PINK1 harbouring PD-causing mutations[3]. We confirm this here in human fibroblasts derived from PINK1 patients with homozygous p.Q456X nonsense (L2122) or p.V170G missense (L1703) mutations[21]. When assessing the integrity of the mitochondrial network scoring fragmented versus elongated mito-RFP labelled mitochondria, no significant differences were observed between control (L2134; L2132) and patient fibroblasts (L1703; L2122) (FIG. 1a, b). However, $\Delta\psi_m$ was significantly decreased in the patient fibroblasts as assessed by the electrochemical potentiometric dye tetramethyl rhodamine ethyl ester (TMRE) (FIG. 1c, d), in line with previous investigations showing bioenergetic abnormalities in mitochondria from PINK1-mutant carriers[21].

Pink1 deficiency in mouse embryonic fibroblast (MEF) cells affects Complex I activity[3]. Since PINK1 is a kinase, we immunocaptured Complex I from isolated mitochondria (FIG. 1e, f) and obtained independent phosphoproteomes from three brain and three liver preparations from mouse, covering 40 out of 46 Complex I subunits (Table I). Eight previously unknown phosphosites were identified in Complex I subunits in wild type brain or liver (not shown), one of which is S250 in NdufA10. Phosphosite Serine 250 in Complex I subunit NdufA10 was found to be dependent on the presence of PINK1.

We next analysed the phosphoproteome of 6 similar preparations of Pink1−/− mice. Remarkably, from all identified phosphosites only Ser250 in Complex I subunit NdufA10 (FIG. 1g) was neither identified in brain nor in liver, whereas the unphosphorylated peptide was identified in 3 out of the 6 samples (not shown). Interestingly, Ser250 is in a site conserved across human, mouse and *Drosophila* (FIG. 1g).

TABLE I

Protein coverage of immunocaptured Complex I subunits.
Complex I was immunocaptured from Pink1+/+ and Pink1−/− mouse brain and liver. The peptide sequences obtained are linked to a specific protein with a 99% confidence interval, and proteins identified at least two out of the three independent experiments in each tissue performed is considered a positive (+) identification. Previously reported human subunits NdufA4L and NdufB1 have no known mouse homologue. Notice that MS analysis covered 40 out of the 46 Complex I subunits.

| Accession no | | | Brain | Liver |
|---|---|---|---|---|
| NADH dehydrogenase (ubiquinone) 1 alpha subcomplex | | | | |
| O35683 | NdufA1 | NADH dehydrogenase (ubiquinone) 1 alpha subcomplex, 1, 7.5 kDa | + | + |
| Q9CQ75 | NdufA2 | NADH dehydrogenase (ubiquinone) 1 alpha subcomplex, 2, 8 kDa | + | + |
| Q9CQ91 | NdufA3 | NADH dehydrogenase (ubiquinone) 1 alpha subcomplex, 3, 9 kDa | + | + |
| Q62425 | NdufA4 | NADH dehydrogenase (ubiquinone) 1 alpha subcomplex, 4, 9 kDa | + | + |
| Q4FZG9 | NdufA4L2 | NADH dehydrogenase (ubiquinone) 1 alpha subcomplex, 4-like 2 | not identified | not identified |
| Q9CPP6 | NdufA5 | NADH dehydrogenase (ubiquinone) 1 alpha subcomplex, 5, 13 kDa | + | + |
| Q9CQZ5 | NdufA6 | NADH dehydrogenase (ubiquinone) 1 alpha subcomplex, 6, 14 kDa | + | + |
| Q9Z1P6 | NdufA7 | NADH dehydrogenase (ubiquinone) 1 alpha subcomplex, 7, 14.5 kDa | + | + |
| Q9DCJ5 | NdufA8 | NADH dehydrogenase (ubiquinone) 1 alpha subcomplex, 8, 19 kDa | + | + |
| Q9DC69 | NdufA9 | NADH dehydrogenase (ubiquinone) 1 alpha subcomplex, 9, 39 kDa | + | + |
| Q99LC3 | NdufA10 | NADH dehydrogenase (ubiquinone) 1 alpha subcomplex, 10, 42 kDa | + | + |
| Q9D8B4 | NdufA11 | NADH dehydrogenase (ubiquinone) 1 alpha subcomplex, 11, 14.7 kDa | + | + |
| Q7TMF3 | NdufA12 | NADH dehydrogenase (ubiquinone) 1 alpha subcomplex, 12 | + | + |
| Q9ERS2 | NdufA13 | NADH dehydrogenase (ubiquinone) 1 alpha subcomplex, 13 | + | + |
| NADH dehydrogenase (ubiquinone) 1 beta subcomplex | | | | |
| Q9CPU2 | NdufB2 | NADH dehydrogenase (ubiquinone) 1 beta subcomplex, 2, 8 kDa | + | + |
| Q9CQZ6 | NdufB3 | NADH dehydrogenase (ubiquinone) 1 beta subcomplex, 3, 12 kDa | + | + |
| Q9CQC7 | NdufB4 | NADH dehydrogenase (ubiquinone) 1 beta subcomplex, 4, 15 kDa | + | + |
| Q9CQH3 | NdufB5 | NADH dehydrogenase (ubiquinone) 1 beta subcomplex, 5, 16 kDa | + | + |
| Q3UIU2 | NdufB6 | NADH dehydrogenase (ubiquinone) 1 beta subcomplex, 6, 17 kDa | + | + |
| Q9CR61 | NdufB7 | NADH dehydrogenase (ubiquinone) 1 beta subcomplex, 7, 18 kDa | + | + |
| Q9D6J5 | NdufB8 | NADH dehydrogenase (ubiquinone) 1 beta subcomplex, 8, 19 kDa | + | + |
| Q9CQJ8 | NdufB9 | NADH dehydrogenase (ubiquinone) 1 beta subcomplex, 9, 22 kDa | + | + |
| Q9DCS9 | NdufB10 | NADH dehydrogenase (ubiquinone) 1 beta subcomplex, 10, 22 kDa | + | + |
| O09111 | NdufB11 | NADH dehydrogenase (ubiquinone) 1 beta subcomplex, 11, 17.3 kDa | + | + |
| NADH dehydrogenase (ubiquinone) 1, subcomplex unknown | | | | |
| Q9CQY9 | NdufC1 | NADH dehydrogenase (ubiquinone) 1, subcomplex unknown, 1, 6 kDa | not identified | not identified |
| Q9CQ54 | NdufC2 | NADH dehydrogenase (ubiquinone) 1, subcomplex unknown, 2, 14.5 kDa | + | + |
| NADH dehydrogenase (ubiquinone) Fe—S protein | | | | |
| Q91VD9 | NdufS1 | NADH dehydrogenase (ubiquinone) Fe—S protein 1, 75 kDa | + | not identified |
| Q91WD5 | NdufS2 | NADH dehydrogenase (ubiquinone) Fe—S protein 2, 49 kDa | + | + |
| Q9DCT3 | NdufS3 | NADH dehydrogenase (ubiquinone) Fe—S protein 3, 30 kDa | + | + |
| Q9CXZ1 | NdufS4 | NADH dehydrogenase (ubiquinone) Fe—S protein 4, 18 kDa | + | + |
| Q99LY9 | NdufS5 | NADH dehydrogenase (ubiquinone) Fe—S protein 5, 15 kDa | + | + |
| P52503 | NdufS6 | NADH dehydrogenase (ubiquinone) Fe—S protein 6, 13 kDa | + | + |
| Q6DC70 | NdufS7 | NADH dehydrogenase (ubiquinone) Fe—S protein 7, 20 kDa | + | + |
| Q8K3J1 | NdufS8 | NADH dehydrogenase (ubiquinone) Fe—S protein 8, 23 kDa | + | + |

TABLE I-continued

Protein coverage of immunocaptured Complex I subunits.
Complex I was immunocaptured from Pink1+/+ and Pink1−/− mouse brain and liver. The peptide sequences obtained are linked to a specific protein with a 99% confidence interval, and proteins identified at least two out of the three independent experiments in each tissue performed is considered a positive (+) identification. Previously reported human subunits NdufA4L and NdufB1 have no known mouse homologue. Notice that MS analysis covered 40 out of the 46 Complex I subunits.

| Accession no | | | Brain | Liver |
|---|---|---|---|---|
| NADH dehydrogenase (ubiquinone) flavoprotein 1 | | | | |
| Q91YT0 | NdufV1 | NADH dehydrogenase (ubiquinone) flavoprotein 1, 51 kDa | + | + |
| Q9D6J6 | NdufV2 | NADH dehydrogenase (ubiquinone) flavoprotein 2, 24 kDa | + | + |
| Q8BK30 | NdufV3 | NADH dehydrogenase (ubiquinone) flavoprotein 3, 10 kDa | + | + |
| Mitochondrially encoded NADH dehydrogenase subunit | | | | |
| P03888 | ND-1 | mitochondrially encoded NADH dehydrogenase subunit 1 | + | + |
| P03893 | ND-2 | mitochondrially encoded NADH dehydrogenase subunit 2 | + | + |
| P03899 | ND-3 | mitochondrially encoded NADH dehydrogenase subunit 3 | + | + |
| P03911 | ND-4 | mitochondrially encoded NADH dehydrogenase subunit 4 | + | + |
| P03903 | ND-4L | mitochondrially encoded NADH dehydrogenase subunit 4L | not identified | not identified |
| P03921 | ND-5 | mitochondrially encoded NADH dehydrogenase subunit 5 | + | + |
| P03925 | ND-6 | mitochondrially encoded NADH dehydrogenase subunit 6 | not identified | not identified |

Example 2. NdufA10 Phosphorylation is Important for Complex I Function

We stably transfected Pink1+/+ and Pink1−/− MEFs with wild type NdufA10$^{wt}$, phosphorylation-deficient NdufA10$^{S250}$ and phosphomimetic NdufA10$^{S250D}$ (FIG. 2a). While the defect in $\Delta\psi_m$ assessed with TMRE dye was not rescued using NdufA10wt or NdufA10S250A, the phosphomimetic NdufA10$^{S250D}$ completely restored $\Delta\psi_m$ to wild type levels (FIG. 2b, c). No effects on $\Delta\psi_m$ were observed in Pink1+/+MEFs expressing the same NdufA10 mutants (FIG. 2b, c). Hence, a phosphomimetic mutation at Ser250 in NdufA10 is sufficient to restore the defect in $\Delta\psi_m$ in Pink1$^{-/-}$ mutant cells.

NdufA10 is located in the subunit Iγ of Complex I in close vicinity to the ND1 and ND3 subunits[22,23]. We therefore hypothesized that the identified phosphorylation site on NdufA10 could structurally influence the ubiquinone binding cavity. We performed colorimetric enzymatic assays for Complex I, in which the substrate NADH is not rate-limiting, to assess the reduction of decylubiquinone, an ubiquinone analogue (FIG. 2d). Reduction of decylubiquinone was significantly affected in Complex I prepared from Pink1$^{-/-}$ MEFs expressing NdufA10wt but was restored in Pink1$^{-/-}$ MEFs expressing NdufA10$^{S250D}$ (FIG. 2e). The effect on Complex I was specific for its ubiquinone reductase enzymatic function since another enzymatic assay that employs only the NADH-binding site of Complex I and which is based on the reduction of the artificial substrate hexamminerithenium (HAR)24 (FIG. 2d) was not affected in Pink1 deficient cells, nor in Pink1$^{-/-}$ or wild type cells expressing NdufA10$^{wt}$, NdufA10$^{S250A}$ or NdufA10$^{S250D}$ (FIG. 2f). These data collectively show that NdufA10 is required for the binding and/or reduction of the physiological Complex I substrate ubiquinone.

Example 3. Restoring NdufA10 Phosphorylation can Restore PD Phenotypes in Drosophila We next assessed to what extent Drosophila pink1 mutant phenotypes could be rescued by expression of wild type (A10$^{wt}$), phosphorylation-deficient (A10$^{SA}$) or phosphomimetic (A10$^{SD}$) NdufA10. Previously we reported that pink1B9 null mutant Drosophila fail to maintain neurotransmitter release at neuromuscular junctions (NMJ) (FIG. 3a) during high frequency stimulation (10 Hz)[3]. However, this decline in neurotransmitter release was almost completely rescued when expressing phosphomimetic A10$^{SD}$, but not with A10$^{wt}$ or A10$^{SA}$ (FIG. 3b). This effect is not due to defects in basal neurotransmitter release efficiency as release during low frequency stimulation in 2 mM external CaCl$_2$ is not affected (FIG. 3c). This neurotransmitter release defect is the consequence of defects in reserve pool (RP) vesicle mobilisation[3], which can be assessed using FM 1-43, a lipophilic dye that internalizes in newly formed synaptic vesicles and upon prolonged stimulation also labels RP vesicles. Uploading of the RP is indeed rescued upon expression of the A10SD mutant in pink1B9 flies (FIG. 3d, e), but not when expressing A10$^{wt}$ or A10$^{SA}$ mutants. We finally assessed $\Delta\psi_m$ in mitochondria at NMJ using JC-1, a green fluorescent potentiometric dye that shifts to red fluorescence as a function of a normal negative $\Delta\psi_m$[25]. Synaptic mitochondria of pink1B9 mutants expressing A10$^{SD}$ showed red JC-1 aggregates comparable to control (FIG. 3f, g), contrary to synaptic mitochondria of pink1B9 mutants expressing A10$^{wt}$ or A10$^{SA}$ which displayed similar signals as the pink1B9 mutant. The $\Delta\psi_m$ was also not disturbed in control pink1rev NMJ expressing NdufA10 mutants (not shown). Thus, this previously identified synaptic phenotype is fully rescued by phosphomimetic NdufA10$^{SD}$.

Example 4. Restoring NdufA10 Phosphorylation can Restore PD-Associated Defects in Mammalian and Patient-Derived Fibroblasts We further scrutinized whether the pathway linking PINK1 to Complex I activity has a pathogenic relevance in humans. Pink1$^{-/-}$ cells expressing human wild type or PINK1 containing PD-causing mutations were stably transduced with NdufA10$^{wt}$, NdufA10$^{S250A}$ and NdufA10$^{S250D}$ respectively (data not shown). NdufA10$^{S250D}$ was able to fully restore the decylubiquinone reduction reaction in Complex I from cells expressing PINK1 clinical mutants G309D and W437X, or the artificial kinase inactive (KD) PINK1 mutant (FIG. 4a), while NdufA10$^{wt}$ and NdufA10$^{S250A}$ had no effect. The functional consequence is clear from $\Delta\psi_m$ measurements which confirm full restoration upon NdufA10$^{S250D}$ expression in the cells expressing the PD-causing mutations (FIG. 4b). Ultimately, we electroporated human fibroblasts derived from PINK1-mutant patients and controls (FIG. 1) with GFP-tagged forms of NdufA10 mutants. The $\Delta\psi_m$ was normalized as assessed by TMRE in the GFP positive patient-derived fibroblasts expressing NdufA10S250D but not those expressing NdufA10wt or NdufA10S250A (FIG. 4c, d). Thus, restoration of the (pseudo)phosphorylation status of NdufA10 rescues Complex I activity in cells harbouring PD-causing mutations in PINK1.

Example 5. Mitochondrial Defects Caused by PINK1 Clinical Mutants Occur in Mutant PINK1 Induced Pluripotent Stem Cells To further scrutinize if the observations obtained from patient skin fibroblasts were phenocopied in a human neuronal cell type, we examined the role of endogenous PINK1 in induced pluripotent stem (iPS) cells from skin fibroblasts taken from two PD patients with nonsense (c.1366C>T; p.Q456X) mutation in the PINK1 gene. These cells were differentiated into neurons according to the previously established protocol[31]. When assessing the mitochondrial membrane potential ($\Delta\psi$m) between control (L2134; L2135) and patient derived iPS cells (L2124; L2122) using the electrochemical potentiometric dye tetramethyl rhodamine ethyl ester (TMRE) we observed a decrease of the $\Delta\psi$m in line with previous investigations showing bioenergetic abnormalities in mitochondria from PINK1-mutant carriers (FIG. 5).

CONCLUSION

Our work demonstrates that phosphorylation of Ser250 in NdufA10 regulates the ubiquinone reductase ability of Complex I. Crystal structures from *Thermus thermophilus* Complex I reveal that the subunits NdufS2 and NdufS7 are involved in electron donation to ubiquinone[26,27], and that the contacts between the peripheral arm and the membrane domain of Complex I are mediated by NdufS2, ND1 and ND3, which leads to the formation of a cavity capable of harbouring the large hydrophobic substrate ubiquinone[22,28]. NdufA10 is located closely to ND1 and ND3 and we, therefore, speculate that phosphorylation of this site regulates the interaction of Complex I with ubiquinone. It should be noted that vitamin K2, an alternative electron carrier for ubiquinone, can rescue the pink1B9 mutant phenotype in *Drosophila*[18], further arguing for a specific effect at the level of the ubiquinone reductase activity of Complex I. From a clinical perspective, it is extremely interesting that mutations in PINK1 known to cause PD apparently affect the phosphorylation of this site, explaining the defects in $\Delta\psi_m$ seen in patient cells. While the most parsimonious explanation for our observations is that PINK1 is directly involved in the phosphorylation of NdufA10, we have not been able to directly demonstrate this with purified enzyme and substrate. Obtaining reproducible in vitro kinase assays with PINK1 has been notoriously challenging and the few substrates that have been identified for PINK1, such as mitochondrial protease Htr2A/OMI29, mitochondrial chaperone TRAP130 and Parkin, cannot explain the disruption of oxidative phosphorylation as shown by our experiments.

We conclude that PINK1 has a dual function in the maintenance of mitochondrial homeostasis. Under steady state conditions, PINK1 maintains a certain degree of phosphorylation to keep Complex I (and ETC) activity in check. When mutated, phosphorylation becomes deficient and ETC function becomes destabilized with latent alteration of $\Delta\psi_m$, which manifests clinically as a late-onset defect in the dopaminergic neurons of the substantia nigra. The cell specificity of the clinical symptomatology remains a tantalizing and unfortunately unexplained issue, but our experiments suggest that patients harbouring PINK1 mutations should be explored for additional subtle phenotypes in organs that strongly depend on oxidative phosphorylation. In any event, our work provides a molecular mechanism for the dysfunction of Complex I in these patients. Bearing in mind that Complex I defects are also commonly observed in sporadic PD patients, therapeutic approaches that rescue Complex I activity by activating phosphorylation or inhibiting dephosphorylation of NdufA10 at residue Ser250 in PINK1 patients might yield excellent candidate drugs to be tested in sporadic cases as well.

REFERENCES

1. Valente, E. M. et al. Hereditary early-onset Parkinson's disease caused by mutations in PINK1. *Science* 304, 1158-1160, doi:10.1126/science.1096284 (2004).
2. Valente, E. M. et al. PINK1 mutations are associated with sporadic early-onset parkinsonism. *Ann Neurol* 56, 336-341, doi:10.1002/ana.20256 (2004).
3. Morais, V. A. et al. Parkinson's disease mutations in PINK1 result in decreased Complex I activity and deficient synaptic function. *EMBO Mol Med* 1, 99-111, doi:10.1002/emmm.200900006 (2009).
4. Parker, W. D., Jr. & Swerdlow, R. H. Mitochondrial dysfunction in idiopathic Parkinson disease. *Am J Hum Genet* 62, 758-762, doi:10.1086/301812 (1998).
5. Abramov, A. Y. et al. Bioenergetic consequences of PINK1 mutations in Parkinson disease. *PLoS ONE* 6, e25622, doi:10.1371/journal.pone.0025622 (2011).
6. Panov, A. et al. Rotenone model of Parkinson disease: multiple brain mitochondria dysfunctions after short term systemic rotenone intoxication. *J Biol Chem* 280, 42026-42035, doi:10.1074/jbc.M508628200 (2005).
7. Heikkila, R. E., Cabbat, F. S., Manzino, L. & Duvoisin, R. C. Effects of 1-methyl-4-phenyl-1,2,5,6-tetrahydropyridine on neostriatal dopamine in mice. *Neuropharmacology* 23, 711-713 (1984).
8. Gautier, C. A., Kitada, T. & Shen, J. Loss of PINK1 causes mitochondrial functional defects and increased sensitivity to oxidative stress. *Proc Nati Acad Sci USA* 105, 11364-11369, doi:10.1073/pnas.0802076105 (2008).
9. Narendra, D. P. et al. PINK1 is selectively stabilized on impaired mitochondria to activate Parkin. *PLoS Biol* 8, e1000298, doi:10.1371/journal.pbio.1000298 (2010).
10. Youle, R. J. & Narendra, D. P. Mechanisms of mitophagy. *Nature reviews. Molecular cell biology* 12, 9-14, doi:10.1038/nrm3028 (2011).
11. Narendra, D. P. & Youle, R. J. Targeting mitochondrial dysfunction: role for PINK1 and Parkin in mitochondrial quality control. *Antioxidants & redox signaling* 14, 1929-1938, doi:10.1089/ars.2010.3799 (2011).
12. Park, J. et al. Mitochondrial dysfunction in *Drosophila* PINK1 mutants is complemented by parkin. *Nature* 441, 1157-1161 (2006).
13. Clark, I. E. et al. *Drosophila* pink1 is required for mitochondrial function and interacts genetically with parkin. *Nature* 441, 1162-1166, doi:10.1038/nature04779 (2006).
14. Yang, Y. et al. Mitochondrial pathology and muscle and dopaminergic neuron degeneration caused by inactivation of *Drosophila* Pink1 is rescued by Parkin. *Proc Natl Acad Sci USA* 103, 10793-10798, doi:10.1073/pnas.0602493103 (2006).
15. Deng, H., Dodson, M. W., Huang, H. & Guo, M. The Parkinson's disease genes pink1 and parkin promote mitochondrial fission and/or inhibit fusion in *Drosophila. Proc Natl Acad Sci USA* 105, 14503-14508, doi:10.1073/pnas.0803998105 (2008).
16. Yang, Y. et al. Pink1 regulates mitochondrial dynamics through interaction with the fission/fusion machinery. *Proc Natl Acad Sci USA* 105, 7070-7075, doi:10.1073/pnas.0711845105 (2008).
17. Vilain, S. et al. The yeast complex I equivalent NADH dehydrogenase rescues pink1 mutants. *PLoS genetics* 8, e1002456, doi:10.1371/journal.pgen.1002456 (2012).
18. Vos, M. et al. Vitamin K2 is a mitochondrial electron carrier that rescues pink1 deficiency. *Science* 336, 1306-1310, doi:10.1126/science.1218632 (2012).
19. Exner, N. et al. Loss-of-function of human PINK1 results in mitochondrial pathology and can be rescued by parkin. *J Neurosci* 27, 12413-12418, doi:10.1523/JNEUROSCI.0719-07.2007 (2007).
20. Lutz, A. K. et al. Loss of parkin or PINK1 function increases Drp1-dependent mitochondrial fragmentation. *J Biol Chem* 284, 22938-22951, doi:10.1074/jbc.M109.035774 (2009).
21. Grunewald, A. et al. Differential effects of PINK1 nonsense and missense mutations on mitochondrial function and morphology. *Exp Neurol* 219, 266-273, doi:10.1016/j.expneurol.2009.05.027 (2009).
22. Efremov, R. G., Baradaran, R. & Sazanov, L. A. The architecture of respiratory complex I. *Nature* 465, 441-445, doi:10.1038/nature09066 (2010).
23. Janssen, R. J., Nijtmans, L. G., van den Heuvel, L. P. & Smeitink, J. A. Mitochondrial complex I: structure, function and pathology. *J Inherit Metab Dis* 29, 499-515, doi:10.1007/s10545-006-0362-4 (2006).
24. Sled, V. D. & Vinogradov, A. D. Kinetics of the mitochondrial NADH-ubiquinone oxidoreductase interaction with hexammineruthenium(III). *Biochim Biophys Acta* 1141, 262-268 (1993).
25. Verstreken, P. et al. Synaptic mitochondria are critical for mobilization of reserve pool vesicles at *Drosophila* neuromuscular junctions. *Neuron* 47, 365-378, doi:10.1016/j.neuron.2005.06.018 (2005).
26. Sazanov, L. A. & Hinchliffe, P. Structure of the hydrophilic domain of respiratory complex I from *Thermus thermophilus. Science* 311, 1430-1436, doi:10.1126/science.1123809 (2006).
27. Berrisford, J. M. & Sazanov, L. A. Structural basis for the mechanism of respiratory complex I. *J Biol Chem* 284, 29773-29783, doi:10.1074/jbc.M109.032144 (2009).
28. Tocilescu, M. A., Zickermann, V., Zwicker, K. & Brandt, U. Quinone binding and reduction by respiratory complex I. *Biochim Biophys Acta* 1797, 1883-1890, doi:10.1016/j.bbabio.2010.05.009 (2010).
29. Plun-Favreau, H. et al. The mitochondrial protease HtrA2 is regulated by Parkinson's disease associated kinase PINK1. *Nat Cell Biol* 9, 1243-1252 (2007).
30. Pridgeon, J. W., Olzmann, J. A., Chin, L. S. & Li, L. PINK1 protects against oxidative stress by phosphorylating mitochondrial chaperone TRAP1. *PLoS Biol* 5, e172, doi:10.1371/journal.pbio.0050172 (2007).
31. Seibler P, Graziotto J, Jeong H, Simunovic F, Klein C, Krainc D. Mitochondrial Parkin recruitment is impaired in neurons derived from mutant PINK1 induced pluripotent stem cells. J Neurosci. 2011; 31(16):5970-6.
32. Hornbeck P V, Kornhauser J M, Tkachev S, Zhang B, Skrzypek E, Murray B, Latham V, Sullivan M. PhosphoSitePlus: a comprehensive resource for investigating the structure and function of experimentally determined post-translational modifications in man and mouse. Nucleic Acids Res. 2012; 40(Data base issue):D261-70.

The invention claimed is:

1. A NdufA10 phosphomimetic mutant or a nucleic acid encoding such phosphomimetic mutant, wherein the phosphomimetic mutation is an S250D mutation at position 250.

2. A screening method for compounds able to restore or increase NdufA10 phosphorylation, comprising contacting a composition comprising the NdufA10 protein or a peptide substrate thereof and a kinase or phosphatase able to affect phosphorylation of NdufA10 at position 250 with a compound, and evaluating phosphorylation status of NdufA10.

3. The method according to claim 2, wherein the kinase is PINK1.

4. A method for treating Parkinson's disease in a subject in need thereof, comprising restoring or mimicking the phosphorylation of NdufA10 at position 250 in said subject, wherein the Parkinson's disease in the subject results from a deficiency of mitochondrial complex protein NduFA10 protein phosphorylation at amino acid position 250.

5. The method according claim 4, wherein the restoring or mimicking is done through gene therapy.

6. The method according to claim 5, wherein the mimicking is done with a nucleic acid encoding an NdufA10 phosphomimetic mutant, wherein the phosphomimetic mutation is at position 250.

7. The method of claim 4, comprising administering an NdufA10 phosphomimetic mutant or a nucleic acid encoding such phosphomimetic mutant to the subject, wherein the phosphomimetic mutation is at position 250.

8. The method of claim 7, wherein the mutation is a S250D mutation.

9. The method of claim 4, wherein the Parkinson's disease is sporadic Parkinson's-disease or Parkinson's characterized by mutations in PINK1.

* * * * *

```
                          SEQUENCE LISTING

<160> NUMBER OF SEQ ID NOS: 10

<210> SEQ ID NO 1
<211> LENGTH: 355
<212> TYPE: PRT
<213> ORGANISM: Homo sapiens

<400> SEQUENCE: 1

Met Ala Leu Arg Leu Leu Lys Leu Ala Ala Thr Ser Ala Ser Ala Arg
1               5                   10                  15

Val Val Ala Ala Gly Ala Gln Arg Val Arg Gly Ile His Ser Ser Val
            20                  25                  30

Gln Cys Lys Leu Arg Tyr Gly Met Trp His Phe Leu Leu Gly Asp Lys
        35                  40                  45

Ala Ser Lys Arg Leu Thr Glu Arg Ser Arg Val Ile Thr Val Asp Gly
    50                  55                  60

Asn Ile Cys Thr Gly Lys Gly Lys Leu Ala Lys Glu Ile Ala Glu Lys
65                  70                  75                  80

Leu Gly Phe Lys His Phe Pro Glu Ala Gly Ile His Tyr Pro Asp Ser
                85                  90                  95

Thr Thr Gly Asp Gly Lys Pro Leu Ala Thr Asp Tyr Asn Gly Asn Cys
            100                 105                 110

Ser Leu Glu Lys Phe Tyr Asp Asp Pro Arg Ser Asn Asp Gly Asn Ser
```

```
            115                 120                 125
Tyr Arg Leu Gln Ser Trp Leu Tyr Ser Ser Arg Leu Leu Gln Tyr Ser
    130                 135                 140

Asp Ala Leu Glu His Leu Leu Thr Thr Gly Gln Gly Val Val Leu Glu
145                 150                 155                 160

Arg Ser Ile Phe Ser Asp Phe Val Phe Leu Glu Ala Met Tyr Asn Gln
                165                 170                 175

Gly Phe Ile Arg Lys Gln Cys Val Asp His Tyr Asn Glu Val Lys Ser
            180                 185                 190

Val Thr Ile Cys Asp Tyr Leu Pro Pro His Leu Val Ile Tyr Ile Asp
        195                 200                 205

Val Pro Val Pro Glu Val Gln Arg Ile Gln Lys Lys Gly Asp Pro
210                 215                 220

His Glu Met Lys Ile Thr Ser Ala Tyr Leu Gln Asp Ile Glu Asn Ala
225                 230                 235                 240

Tyr Lys Lys Thr Phe Leu Pro Glu Met Ser Glu Lys Cys Glu Val Leu
                245                 250                 255

Gln Tyr Ser Ala Arg Glu Ala Gln Asp Ser Lys Lys Val Val Glu Asp
            260                 265                 270

Ile Glu Tyr Leu Lys Phe Asp Lys Gly Pro Trp Leu Lys Gln Asp Asn
        275                 280                 285

Arg Thr Leu Tyr His Leu Arg Leu Leu Val Gln Asp Lys Phe Glu Val
    290                 295                 300

Leu Asn Tyr Thr Ser Ile Pro Ile Phe Leu Pro Glu Val Thr Ile Gly
305                 310                 315                 320

Ala His Gln Thr Asp Arg Val Leu His Gln Phe Arg Glu Leu Pro Gly
                325                 330                 335

Arg Lys Tyr Ser Pro Gly Tyr Asn Thr Glu Val Gly Asp Lys Trp Ile
            340                 345                 350

Trp Leu Lys
        355

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
cagaattcca aaatgaccgc cgtgttccgc g                               31

<210> SEQ ID NO 3
<211> LENGTH: 56
<212> TYPE: DNA
<213> ORGANISM: Artificial Sequence
<220> FEATURE:
<223> OTHER INFORMATION: Primer

<400> SEQUENCE: 3
gtgcggccgc ctagtggtga tggtgatgat ggatgccctg gttgatgcct attttc    56

<210> SEQ ID NO 4
<211> LENGTH: 23
<212> TYPE: DNA
<213> ORGANISM: Artificial Sequence
<220> FEATURE:
<223> OTHER INFORMATION: Primer
```

```
<400> SEQUENCE: 4
cggcatgggt ggcgatgtcc ttg                                              23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
caaggacatc gccacccatg ccg                                              23

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cggcatgggt gtcgatgtcc ttg                                              23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
caaggacatc gacacccatg ccg                                              23

<210> SEQ ID NO 8
<211> LENGTH: 35
<212> TYPE: PRT
<213> ORGANISM: Homo sapiens

<400> SEQUENCE: 8

Ile Thr Ser Ala Tyr Leu Gln Asp Ile Glu Asn Ala Tyr Lys Lys Thr
 1               5                  10                  15

Phe Leu Pro Glu Met Ser Glu Lys Cys Glu Val Leu Gln Tyr Ser Ala
            20                  25                  30

Arg Glu Ala
        35

<210> SEQ ID NO 9
<211> LENGTH: 35
<212> TYPE: PRT
<213> ORGANISM: Mus musculus

<400> SEQUENCE: 9

Val Thr Ser Ala Tyr Leu Gln Asp Ile Glu Asn Ala Tyr Lys Lys Thr
 1               5                  10                  15

Phe Leu Pro Lys Met Ser Glu Met Cys Glu Val Leu Val Tyr Asp Ser
            20                  25                  30

Trp Glu Ala
        35

<210> SEQ ID NO 10
<211> LENGTH: 37
<212> TYPE: PRT
<213> ORGANISM: Drosophila melanogaster
```

```
<400> SEQUENCE: 10

Lys Val Phe Ser Asp Ala Tyr Leu Ser Asp Leu Glu Gln Leu Tyr Lys
1               5                   10                  15

Gln Gln Tyr Leu Lys Asp Ile Ser Thr His Ala Glu Leu Leu Ile Tyr
            20                  25                  30

Asp Trp Thr Ala Gly
            35
```